(12) United States Patent
Huang et al.

(10) Patent No.: US 10,729,668 B2
(45) Date of Patent: Aug. 4, 2020

(54) KETOBUTYRATE COMPOUNDS AND COMPOSITIONS FOR TREATING AGE-RELATED SYMPTOMS AND DISEASES

(71) Applicant: The Regents of the University of California, Oakland, CA (US)

(72) Inventors: Jing Huang, Los Angeles, CA (US); Randall M. Chin, Van Nuys, CA (US); Xudong Fu, Los Angeles, CA (US); Heejun Hwang, Los Angeles, CA (US); Karen Reue, Torrance, CA (US); Laurent Vergnes, Los Angeles, CA (US); Meisheng Jiang, Los Angeles, CA (US); Brett E. Lomenick, Los Angeles, CA (US); Xiang Yin, Los Angeles, CA (US); Mansoureh Eghbali, Los Angeles, CA (US); Jingyuan Li, Los Angeles, CA (US); Samuel Wheeler French, Los Angeles, CA (US); Ronik Khachatoorian, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 15/319,589

(22) PCT Filed: Jun. 29, 2015

(86) PCT No.: PCT/US2015/038227
§ 371 (c)(1),
(2) Date: Dec. 16, 2016

(87) PCT Pub. No.: WO2016/003854
PCT Pub. Date: Jan. 7, 2016

(65) Prior Publication Data
US 2017/0128395 A1 May 11, 2017

Related U.S. Application Data

(60) Provisional application No. 62/019,055, filed on Jun. 30, 2014.

(51) Int. Cl.
*A61K 31/19* (2006.01)
(52) U.S. Cl.
CPC .................................. *A61K 31/19* (2013.01)
(58) Field of Classification Search
None
See application file for complete search history.

(56) References Cited

U.S. PATENT DOCUMENTS

| 6,149,924 A | 11/2000 | Paul |
| 2004/0127413 A1 | 7/2004 | Plouvier et al. |

(Continued)

FOREIGN PATENT DOCUMENTS

| JP | 2003518477 A | 6/2003 |
| JP | 2008512462 A | 4/2008 |

(Continued)

OTHER PUBLICATIONS

Watabe et al., Mol Pharmacol 74:933-940, 2008.*
Mayer et al., J Am Coll Cardiol. Mar. 1, 1996;27(3):517-27.*
Angeline et al., Indian J Clin Biochem. Jan. 2005; 20(1): 18-20.*
Landgren et al., J Intern Med. Apr. 1995;237(4):381-8.*
Muthuramu et al., PLOS ONE, vol. 8, Issue 5, pp. 1-11.*
Al-Obaidi et al., Journal of the American College of Cardiology, vol. 36, No. 4, 2000, pp. 1217-1222.*
International Search Report received in PCT/US2015/038227, dated Sep. 29, 2015.

(Continued)

*Primary Examiner* — Karl J Puttlitz
(74) *Attorney, Agent, or Firm* — Suzannah K. Sundby, Esq.; Canady + Lortz LLP

(57) ABSTRACT

Disclosed herein are methods for (a) treating, inhibiting, or reducing aging of a subject, (b) treating, inhibiting, or reducing an age-related symptom or an age-related disease in a subject, and/or (c) increasing the lifespan of a subject which comprise administering to the subject one or more ketobutyrate compounds and compositions thereof.

12 Claims, 15 Drawing Sheets

(56) References Cited

U.S. PATENT DOCUMENTS

| | | | |
|---|---|---|---|
| 2005/0107415 A1 | 5/2005 | Wu et al. | |
| 2005/0197397 A1* | 9/2005 | Martin | A61K 31/19 514/557 |
| 2006/0252699 A1* | 11/2006 | Guttuso, Jr. | A61K 31/19 514/21.9 |
| 2008/0275111 A1 | 11/2008 | Hwang et al. | |
| 2009/0130051 A1 | 5/2009 | Jarrott | |
| 2009/0214382 A1* | 8/2009 | Burgess | A01N 37/42 422/22 |
| 2011/0288153 A1 | 11/2011 | Huang et al. | |
| 2012/0022425 A1 | 1/2012 | Yeung et al. | |
| 2012/0214804 A1 | 8/2012 | Kim | |

FOREIGN PATENT DOCUMENTS

| | | | |
|---|---|---|---|
| JP | 2008530115 A | 8/2008 | |
| JP | 2008532951 A | 8/2008 | |
| JP | 2008534582 A | 11/2008 | |
| JP | 2013508452 A | 3/2013 | |
| WO | 0136454 A1 | 5/2001 | |

OTHER PUBLICATIONS

Written Opinion received in PCT/US2015/038227, dated Sep. 29, 2015.
Examination Report No. 1 received in AU2015284409 dated Aug. 22, 2019.
Office Action received in CN 201580035440, dated Dec. 6, 2019.
Office Action received in JP2016574149, dated Nov. 28, 2019.
Notice of Reasons for Refusal received in JP 2016-574149 dated Apr. 17, 2019.
O'Donnell-Tormey et al., "Secretion of pyruvate. An antioxidant defense of cells", Feb. 1, 1987, pp. 500-514, vol. 165, Publisher: The Journal of experimental medicine.
Extended European Search Report received in EP20150815637 dated Jan. 5, 2018.
Salminen, et al., "Krebs cycle intermediates regulate DNA and histone methylation: Epigenetic impact on the aging process", Jun. 5, 2014, p. 45-65, vol. 16, Publisher: Ageing Research Reviews.
First Office Action and Search Report received in CN 201580035440, dated Dec. 26, 2018.

* cited by examiner

KETOBUTYRATE COMPOUNDS AND COMPOSITIONS FOR TREATING AGE-RELATED SYMPTOMS AND DISEASES

CROSS-REFERENCE TO RELATED APPLICATIONS

This application claims the benefit of U.S. Application No. 62/019,055, filed Jun. 30, 2014, which is herein incorporated by reference in its entirety.

BACKGROUND OF THE INVENTION

1. Field of the Invention

The present invention relates to treating, inhibiting, or reducing aging and age-related symptoms and diseases.

2. Description of the Related Art

Metabolism and aging are intimately linked. Compared to ad libitum feeding, dietary restriction (DR) or calorie restriction (CR) consistently extends lifespan and delays age-related diseases in evolutionarily diverse organisms. Similar conditions of nutrient limitation and genetic or pharmacological perturbations of nutrient or energy metabolism also have longevity benefits. Several compounds that modulate aging with largely undefined molecular mechanisms have been identified.

However, a need still exists for treatments for age-related symptoms and age-related diseases including cancer, diabetes, and cardiovascular disease, and extending the lifespans of subjects.

SUMMARY OF THE INVENTION

In some embodiments, the present invention provides methods for treating, inhibiting, or reducing aging, an age-related symptom, and/or an age-related disease in a subject which comprises administering to the subject a therapeutically effective amount of a compound that inhibits NADH dehydrogenase. In some embodiments, the compound is a ketobutyrate compound. In some embodiments, the compound is alpha-ketobutyrate or alpha-ketobutyric acid. In some embodiments, the therapeutically effective amount of the ketobutyrate compound is less than the amount of alpha-ketoglutarate needed to produce the same observable difference. See Chin, et al., (2014) Nature 510:397-401 and the Extended Data Figures related thereto, which is herein incorporated by reference in its entirety. In some embodiments, the therapeutically effective amount of the ketobutyrate compound is less than half the amount of alpha-ketoglutarate needed to produce the same observable difference. In some embodiments, the therapeutically effective amount of the ketobutyrate compound is about $\frac{1}{16}$ the amount of alpha-ketoglutarate needed to produce the same observable difference. In some embodiments, the therapeutically effective amount of the ketobutyrate compound is administered as several doses over a given period of time, e.g., a daily dose for a week or more. In some embodiments, the ketobutyrate compound is administered as a daily dose of about 0.01-1.0, preferably about 0.01-0.5, more preferably about 0.1-0.2 grams per kilogram body weight per day. In some embodiments, about 0.05 to about 2 grams of the ketobutyrate compound per kilogram weight of the subject is administered to the subject daily for at least a week. In some embodiments, the methods comprise increasing the alpha-ketobutyrate levels in the subject by about 30-60%, about 45-55%, or about 50%. In some embodiments, the age-related symptom is cholesterol build-up, stiffening of arterial walls, increased blood pressure, immunosenescence, muscle loss, bone loss, arthritis, osteoporosis, memory loss, hearing loss, visual decline, increased wrinkles, hair loss, hair thinning, hair graying, decreased stress resistance, dementia, loss of hearing, loss of vision, loss of mobility, loss of muscle strength, loss of stamina, frailty, fatigue, increased susceptibility to infection, dry skin, wrinkled skin, altered sleep patterns, altered circadian cycles, metabolic changes, biochemical changes, or the like. In some embodiments, the age-related symptom is hair loss, hair thinning, hair graying, loss of mobility, loss of stamina, fatigue, increased susceptibility to infection, a metabolic change, or a biochemical change. In some embodiments, the age-related disease is a cancer (e.g., gliomas, leukemia, lymphoma, breast cancer, prostate cancer, lung cancer, etc.), a neurodegenerative disease (e.g., Parkinson's disease, Alzheimer's disease, Huntington's disease, dementia, etc.), sarcopenia, osteopenia, osteoporosis, arthritis, atherosclerosis, cardiovascular disease, hypertension, cataracts, presbyopia, glaucoma, type 2 diabetes, metabolic syndrome, alopecia, chronic inflammation, immunosenescence, or the like, or an age-related condition such as cardiac hypertrophy, cardiomyopathy, heart failure, or cardiovascular disease. In some embodiments, the age-related disease is cardiac hypertrophy, heart failure, myocardial infarction, ischemia reperfusion injury, or Alzheimer's Disease. In some embodiments, the lifespan of the subject is extended by up to about 10%, 30%, 40%, 50%, 60%, or 70% as compared to untreated control subjects.

In some embodiments, the present invention provides a ketobutyrate compound for use in treating, inhibiting, or reducing aging of a subject; treating, inhibiting, or reducing an age-related symptom in a subject; treating, inhibiting, or reducing an age-related disease in a subject; increasing the lifespan of a subject; or treating, inhibiting, or reducing cardiac hypertrophy and/or myocardial infarction in a subject. In some embodiments, the ketobutyrate compound is alpha-ketobutyrate or alpha-ketobutyric acid. In some embodiments, the age-related symptom is cholesterol build-up, stiffening of arterial walls, increased blood pressure, immunosenescence, muscle loss, bone loss, arthritis, osteoporosis, memory loss, hearing loss, visual decline, increased wrinkles, hair loss, hair thinning, hair graying, decreased stress resistance, dementia, loss of hearing, loss of vision, loss of mobility, loss of muscle strength, loss of stamina, frailty, fatigue, increased susceptibility to infection, dry skin, wrinkled skin, altered sleep patterns, altered circadian cycles, metabolic changes, biochemical changes, or the like. In some embodiments, the age-related symptom is hair loss, hair thinning, hair graying, loss of mobility, loss of stamina, fatigue, increased susceptibility to infection, a metabolic change, or a biochemical change. In some embodiments, the age-related disease is a cancer (e.g., gliomas, leukemia, lymphoma, breast cancer, prostate cancer, lung cancer, etc.), a neurodegenerative disease (e.g., Parkinson's disease, Alzheimer's disease, Huntington's disease, dementia, etc.), sarcopenia, osteopenia, osteoporosis, arthritis, atherosclerosis, cardiovascular disease, hypertension, cataracts, presbyopia, glaucoma, type 2 diabetes, metabolic syndrome, alopecia, chronic inflammation, immunosenescence, or the like, or an age-related condition such as cardiac hypertrophy, cardiomyopathy, heart failure, or cardiovascular disease. In some embodiments, the age-related disease is cardiac hypertrophy, heart failure, myocardial infarction, ischemia reperfusion injury, or Alzheimer's Disease.

In some embodiments, the present invention provides a composition comprising a purified and/or concentrated amount of one or more ketobutyrate compounds and a pharmaceutically acceptable carrier or foodstuff. In some embodiments, the level of purification or concentration in the composition is not one that is naturally found in nature. In some embodiments, the carrier or foodstuff is not found associated with the one or more ketobutyrate compounds in nature. For example, in some embodiments, the present invention provides a foodstuff, such as milk or orange juice, having one or more ketobutyrate compounds added thereto. In some embodiments, the compositions further comprise at least one ketoglutarate compound such as α-ketoglutarate (α-ketoglutarate), derivatives of α-ketoglutarate (e.g., the derivatives set forth in MacKenzie, et al. (2007) Mol Cell Biol 27(9):3282-3289)), analogues of α-ketoglutarate (e.g., phosphonate analogues (e.g., those recited in Bunik, et al. (2005) Biochemistry 44(31):10552-61), esters of α-ketoglutarate (e.g., dimethyl α-ketoglutarate and octyl α-ketoglutarate), and various species specific analogues, e.g., human α-ketoglutarate, porcine α-ketoglutarate, murine α-ketoglutarate, bovine α-ketoglutarate, and the like. In some embodiments, the amounts of the one or more ketobutyrate compounds and the ketoglutarate compound are present in amounts not found in nature.

In some embodiments, the present invention provides medicaments and methods of making medicaments for treating, inhibiting, or reducing aging, an age-related symptom, and/or an age-related disease in a subject or extending the lifespan of the subject, said medicaments comprise a therapeutically effective amount of a ketobutyrate compound. In some embodiments, the compound is alpha-ketobutyrate or alpha-ketobutyric acid.

In some embodiments, the present invention provides use of one or more ketobutryate compounds in the manufacture of a medicament for treating, inhibiting, or reducing aging, an age-related symptom, and/or an age-related disease in a subject or extending the lifespan of the subject. In some embodiments, the medicaments comprise a therapeutically effective amount of a ketobutyrate compound. In some embodiments, the compound is alpha-ketobutyrate or alpha-ketobutyric acid.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIG. 9A shows the experimental schematics. The LAD is occluded in male mice for 30 minutes followed by a 24 hour reperfusion. At the onset of reperfusion one bolus of α-KB or PBS was applied via tail vein.

FIG. 9B shows the percentage of area at risk (AAR) divided by LV.

FIG. 9C shows the infarct size (IS) divided by AAR.

FIG. 10, right, shows the infarct size resulting from treatment with the indicated compounds before reperfusion. The pictures are inverse color images for better reproducibility.

DETAILED DESCRIPTION OF THE INVENTION

Figure 1:
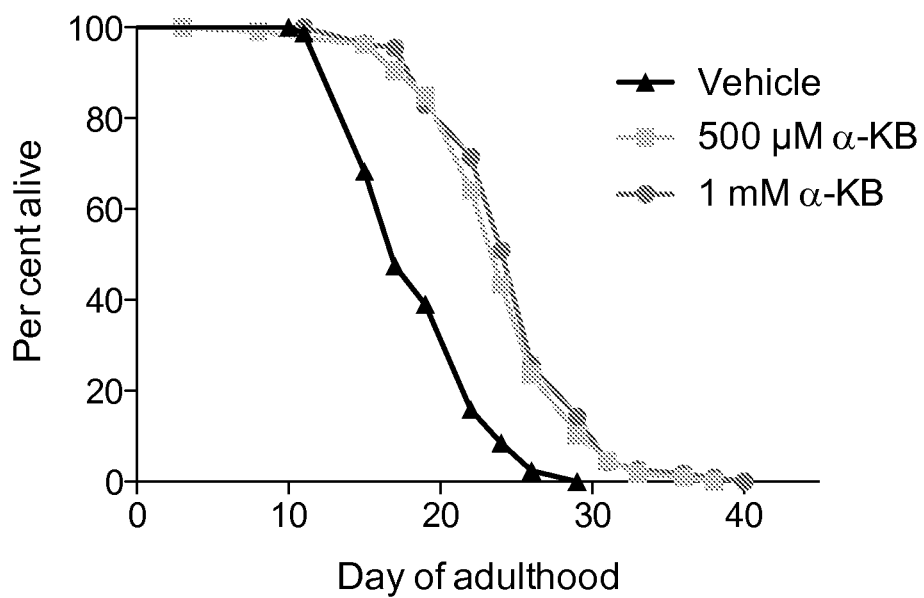
FIG. 1 shows that α-KB extends the lifespan of subjects as compared to the average lifespan of untreated control subjects.

Several small molecules were screened using a model organism for aging, *Caenorhabditis elegans*, to identify compounds that promote longevity and counter aging and age-related diseases. As disclosed herein, one molecule, α-ketobutyrate (α-KB), unexpectedly extended the mean lifespan of *C. elegans* at a significantly lower amount as compared to α-ketoglutarate (α-KG).

α-KB is a keto acid involved in amino acid catabolism and succinyl CoA synthesis. Using isolated mitochondria coupling and electron flow assays, it was found that α-KB engages a distinct molecular target in vivo by inhibiting NADH dehydrogenase (Complex I of the electron transport chain). Unlike α-KG, α-KB does not inhibit either ATP synthase or TOR (target of rapamycin). It was also found that both genetic mutations (e.g., knockdown) and pharmacological perturbation of NADH dehydrogenase extend lifespan in *C. elegans*. Additionally, it was found that α-KB inhibits cellular respiration and induces reactive oxygen species (ROS).

Therefore, in some embodiments, the present invention is directed to methods for treating, inhibiting, or reducing aging, age-related symptoms, and/or age-related diseases in a subject which comprises administering the subject at least one ketobutyrate compound. In some embodiments, the present invention is directed to methods for increasing the lifespan of a subject which comprises administering the subject at least one ketobutyrate compound. In some embodiments, the present invention is directed to compositions for treating, inhibiting, or reducing aging, age-related symptoms, and/or age-related diseases in a subject, said compositions comprise at least one ketobutyrate compound. In some embodiments, the present invention is directed to compositions for increasing the lifespan of a subject, said compositions comprise at least one ketobutyrate compound. In some embodiments, the subject is an animal, which may or may not be an animal model of aging, an age-related symptom, and/or an age-related disease. In some embodiments, the subject is a nematode, a rodent, or a non-human primate. In some embodiments, the subject is a human.

As used herein, "age-related symptoms" refers to biological and/or physical symptoms resulting from aging and includes cholesterol build-up, stiffening of arterial walls, increased blood pressure, immunosenescence, muscle loss, bone loss, arthritis, osteoporosis, memory loss, hearing loss, visual decline, increased wrinkles, hair loss, hair thinning, hair graying, decreased stress resistance, dementia, loss of hearing, loss of vision, loss of mobility, loss of muscle strength, loss of stamina, frailty, fatigue, increased susceptibility to infection, dry skin, wrinkled skin, altered sleep patterns, altered circadian cycles, metabolic changes, biochemical changes, and the like. Metabolic and/or biochemical changes can be evidenced by various biomarkers known in the art. In some embodiments, an age-related symptom refers to an increase in biomarkers indicative of untreated control subjects who are aging. In some embodiments, an age-related symptom refers to an increase in biomarkers indicative of untreated control subjects who are aged. In some embodiments, an age-related symptom refers to a biomarker profile indicative of untreated control subjects who are aging. In some embodiments, an age-related symptom refers to a biomarker profile indicative of untreated control subjects who are aged. Biomarkers and biomarker profiles that are indicative of a subject who is aging and/or an aged subject include atrial natriuretic factor (ANF), B-type natriuretic peptide (BNP), and those as set forth in US20080124752, which is herein incorporated by reference in its entirety.

As used herein, a subject who is "aging" refers to a subject in the period of life when untreated control subjects begin to physically, mentally, and/or biologically deteriorate. In some embodiments, a subject who is aging is one whose chronological age is at least at the median point of the average lifespan of untreated control subjects.

As used herein, an "aged" subject is one whose chronological age is at least two-thirds the average life expectancy of untreated control subjects. For example, if the average life expectancy of a given strain of a laboratory mouse is 2 years, an aged mouse of that strain is at least 16 months, and if the average life expectancy of another strain of laboratory mouse is 3 years, an aged mouse of that strain is 24 months. For humans, if the average life expectancy of a human is about 80 years, an aged human is about 53 years. It should be noted that a subject who is aging may or may not be an aged subject.

As used herein, "age-related diseases" refers to diseases and disorders often associated with aging and includes cancers (e.g., gliomas, leukemia, lymphoma, breast cancer, prostate cancer, lung cancer, etc.), neurodegenerative diseases (e.g., Parkinson's disease, Alzheimer's disease, Huntington's disease, dementia, etc.), sarcopenia, osteopenia, osteoporosis, arthritis, atherosclerosis, cardiovascular disease, hypertension, cataracts, presbyopia, glaucoma, type 2 diabetes, metabolic syndrome, alopecia, chronic inflammation, immunosenescence, and the like. As used herein, an "age-related heart condition" refers to cardiac hypertrophy, cardiomyopathy, heart failure, and cardiovascular disease.

In some embodiments, methods and compositions of the present invention that treat, inhibit, or reduce "aging" in subjects are those that treat, inhibit, or reduce age-related symptoms as compared to untreated control subjects. In some embodiments, methods and compositions of the present invention that treat, inhibit, or reduce "aging" in subjects are those that result in clinical improvement in the clinical symptoms of an age-related disease in a subject as compared to untreated control subjects and/or as compared to the base-line of the subjects prior to treatment. In some embodiments, methods and compositions that treat, inhibit, or reduce "aging" in subjects are those that result in a subject having a biological age and/or a metabolic age that is typical of untreated control subjects who are chronologically younger than the treated subject. In some embodiments, methods and compositions that treat, inhibit, or reduce "aging" in subjects are those that result in a decrease in the biological age and/or metabolic age of the subject as compared to the biological age and/or metabolic age of the subject before treatment. Methods for measuring a subject's biological age and/or metabolic age and comparing to one's chronological age are known in the art. See, for example, U.S. Pat. No. 7,273,453 and US 20080124752, which are herein incorporated by reference in their entirety. In some embodiments, methods and compositions that increase the "lifespan" of subjects are those that result in a subject having a lifespan that is longer than the average lifespan of untreated control subjects.

As used herein, "ketobutyrate compounds" include α-ketobutyrate, α-ketobutyric acid, and compounds having the following structural formula I:

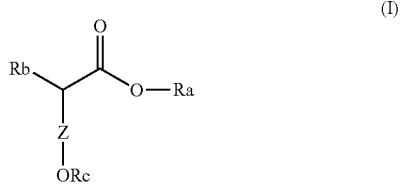

wherein

Ra is a negative charge, H, —CH$_3$, —CH$_2$—CH$_3$, a straight or branched C1-C3 alkyl, a straight or branched C1-C4 alkyl, a straight or branched C1-C5 alkyl, a straight or branched C1-C4 alkyl, —CH$_2$=CH$_3$, a straight or branched C1-C3 alkenyl, a straight or branched C1-C4 alkenyl, a straight or branched C1-C5 alkenyl, or a straight or branched C1-C10 alkenyl, Rb is H, —CH$_3$, —CH$_2$—CH$_3$, a straight or branched C1-C3 alkyl, a straight or branched C1-C4 alkyl, a straight or branched C1-C5 alkyl, a straight or branched C1-C10 alkyl, —CH$_2$=CH$_3$, a straight or branched C1-C3 alkenyl, a straight or branched C1-C4 alkenyl, a straight or branched C1-C5 alkenyl, or a straight or branched C1-C10 alkenyl, Rc is optionally present, and if present, Rc is H, —CH$_3$, —CH$_2$—CH$_3$, a straight or branched C1-C3 alkyl, a straight or branched C1-C4 alkyl, a straight or branched C1-C5 alkyl, a straight or branched C1-C10 alkyl, —CH$_2$=CH$_3$, a straight or branched C1-C3 alkenyl, a straight or branched C1-C4 alkenyl, a straight or branched C1-C5 alkenyl, or a straight or branched C1-C10 alkenyl, and if absent, Z is a double bond, and pharmaceutically acceptable solvates, salts, prodrugs, and metabolites thereof.

In some embodiments, Ra is a negative charge, H, or —CH$_3$. In some embodiments, Rb is H, —CH$_3$, —CH$_2$—CH$_3$, a straight or branched C1-C3 alkyl, —CH$_2$=CH$_3$, or a straight or branched C1-C3 alkenyl. In some embodiments, Z is a double bond. In some embodiments, Ra is a negative charge, H, or —CH$_3$ and Rb is H, —CH$_3$, —CH$_2$—CH$_3$, a straight or branched C1-C3 alkyl, a straight or branched C1-C4 alkyl, a straight or branched C1-C5 alkyl, a straight or branched C1-C10 alkyl, —CH$_2$=CH$_3$, a straight or branched C1-C3 alkenyl, a straight or branched C1-C4 alkenyl, a straight or branched C1-C5 alkenyl, or a straight or branched C1-C10 alkenyl. In some embodiments, Ra is a negative charge, H, or —CH$_3$ and Rb is H, —CH$_3$, —CH$_2$—CH$_3$, a straight or branched C1-C3 alkyl, —CH$_2$=CH$_3$, or a straight or branched C1-C3 alkenyl. In some embodiments, Ra is a negative charge, H, or —CH$_3$, Rb is H, —CH$_3$, —CH$_2$—CH$_3$, a straight or branched C1-C3 alkyl, —CH$_2$=CH$_3$, or a straight or branched C1-C3 alkenyl, and Z is a double bond.

As used herein, a "C1-Cn alkyl" refers to an alkyl having 1-n carbon atoms, where "n" is a positive integer. Similarly, a "C1-Cn alkenyl" refers to an alkenyl having 1-n carbon atoms, where "n" is a positive integer. The alkyls and alkenyls as set forth for Formula I may be substituted or unsubstituted with one or more suitable functional groups that may increase or decrease, but not completely abrogate the ability of the compound to inhibit or reduce the activity NADH dehydrogenase.

As used herein, the abbreviation "KB" may be used to refer to the term "ketobutyrate", e.g., α-ketobutyrate is abbreviated as α-KB. Ketobutyrate compounds also include various species specific analogues. For example, unless explicitly specified as being of a particular species, "α-KB" includes human α-ketobutyrate, porcine α-ketobutyrate, murine α-ketobutyrate, bovine α-ketobutyrate, and the like.

A "pharmaceutically acceptable solvate" refers to a solvate form of a specified compound that retains the biological effectiveness of such compound. Examples of solvates include compounds of the invention in combination with water, isopropanol, ethanol, methanol, dimethyl sulfoxide, ethyl acetate, acetic acid, ethanolamine, or acetone. Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of compounds of Formula I are within the scope of the invention. It will also be appreciated by those skilled in organic chemistry that many organic compounds can exist in more than one crystalline form. For example, crystalline form may vary from solvate to solvate. Thus, all crystalline forms of the compounds of Formula I or the pharmaceutically acceptable solvates thereof are within the scope of the present invention.

The term "pharmaceutically acceptable salts" refers to salt forms that are pharmacologically acceptable and substantially non-toxic to the subject being treated with the compound of the invention. Pharmaceutically acceptable salts include conventional acid-addition salts or base-addition salts formed from suitable non-toxic organic or inorganic acids or inorganic bases. Exemplary acid-addition salts include those derived from inorganic acids such as hydrochloric acid, hydrobromic acid, hydroiodic acid, sulfuric acid, sulfamic acid, phosphoric acid, and nitric acid, and those derived from organic acids such as p-toluenesulfonic acid, methanesulfonic acid, ethane-disulfonic acid, isethionic acid, oxalic acid, p-bromophenylsulfonic acid, carbonic acid, succinic acid, citric acid, benzoic acid, 2-acetoxybenzoic acid, acetic acid, phenylacetic acid, propionic acid, glycolic acid, stearic acid, lactic acid, malic acid, tartaric acid, ascorbic acid, maleic acid, hydroxymaleic acid, glutamic acid, salicylic acid, sulfanilic acid, and fumaric acid. Exemplary base-addition salts include those derived from ammonium hydroxides (e.g., a quaternary ammonium hydroxide such as tetramethylammonium hydroxide), those derived from inorganic bases such as alkali or alkaline earth-metal (e.g., sodium, potassium, lithium, calcium, or magnesium) hydroxides, and those derived from non-toxic organic bases such as basic amino acids.

"A pharmaceutically acceptable prodrug" is a compound that may be converted under physiological conditions or by solvolysis to the specified compound or to a pharmaceutically acceptable salt of such compound. "A pharmaceutically active metabolite" refers to a pharmacologically active product produced through metabolism in the body of a specified compound or salt thereof. Prodrugs and active metabolites of a compound may be identified using routine techniques known in the art. See, e.g., Bertolini, G. et al., (1997) J. Med. Chem. 40:2011-2016; Shan, D. et al., J. Pharm. Sci., 86(7):765-767; Bagshawe K., (1995) Drug Dev. Res. 34:220-230; Bodor, N., (1984) Advances in Drug Res.

13:224-331; Bundgaard, H., Design of Prodrugs (Elsevier Press, 1985) and Larsen, I. K., Design and Application of Prodrugs, Drug Design and Development (Krogsgaard-Larsen et al., eds., Harwood Academic Publishers, 1991).

In some embodiments, the amount of the ketobutyrate compound administered to the subject is a therapeutically effective amount. A "therapeutically effective amount", refers to an amount of one or more compounds of the present invention that, when administered to a subject, (i) treats or inhibits the particular disease, condition, or disorder, (ii) attenuates, ameliorates, or eliminates one or more symptoms of the particular disease, condition, or disorder, and/or (iii) inhibits or delays the onset of one or more symptoms of the particular disease, condition, or disorder, as compared to a control. A therapeutically effective amount of one or more compounds of the present invention will vary depending upon factors such as the given compound(s), the pharmaceutical formulation, route of administration, the type of disease or disorder, the degree of the disease or disorder, and the identity of the subject being treated, but can nevertheless be readily determined by one skilled in the art. For example, in some embodiments, a "therapeutically effective amount" of one or more ketobutyrate compounds is an amount that treats, inhibits, or reduces aging in a subject. In some embodiments, a "therapeutically effective amount" of one or more ketobutyrate compounds is an amount that treats, inhibits, or reduces one or more age-related symptoms in a subject. In some embodiments, a "therapeutically effective amount" of one or more ketobutyrate compounds is an amount that treats, inhibits, or reduces one or more age-related diseases in a subject. In some embodiments, a "therapeutically effective amount" of one or more ketobutyrate compounds is an amount that increases the lifespan of a subject.

In some embodiments, a therapeutically effective amount of the one or more ketobutyrate compounds is administered as a daily dose of about 0.01-2, about 0.25-2, about 0.5-2, about 1-2, or about 2 grams per kilogram weight of the subject per day. As disclosed herein, $\alpha$-KB is about 1-fold more potent than $\alpha$-KG in treating, inhibiting, or reducing aging and age-related symptoms. Therefore, in some embodiments, a therapeutically effective amount of the one or more ketobutyrate compounds is administered as a daily dose of about 0.1-1, about 0.25-1, about 0.5-1, or about 1 gram per kilogram weight of the subject per day. In some embodiments, one or more ketobutyrate compounds is administered as a daily dose of about 0.01-1.0, about 0.01-0.5, or about 0.1-0.2 grams per kilogram weight of the subject per day. The skilled artisan will appreciate that certain factors may influence the dosage required to effectively treat a subject, including but not limited to the severity of the disease or disorder, previous treatments, the general health and/or age of the subject, and other diseases present. In some embodiments, the amount of the one or more ketobutyrate compounds administered to a subject is one that results in about a 10-50%, about a 20-50%, about a 30-50%, or about a 40-50%, increase in $\alpha$-KB levels in the subject. In some embodiments, the amount of the one or more ketobutyrate compounds administered to a subject is one that results in about a 25% increase in $\alpha$-KB levels in the subject. In some embodiments, the amount of the one or more ketobutyrate compounds administered to a subject is one that results in about a 50% increase in $\alpha$-KB levels in the subject.

The therapeutically effective amount may be administered as a single dose or as multiple doses over a period of time. For example, a subject may be treated with one or more ketobutyrate compounds at least once. However, the subject may be treated with the one or more ketobutyrate compounds from about one time per week to about once daily for a given treatment period. The length of the treatment period will depend on a variety of factors such as the severity of the disease or disorder, the concentration and activity of the one or more compounds of the present invention, or a combination thereof. It will also be appreciated that the effective dosage of the one or more compounds used for treatment may increase or decrease over the course of a particular treatment.

The one or more ketobutyrate compounds to be administered to a subject may be provided as a pharmaceutical formulation. Pharmaceutical formulations may be prepared in a unit-dosage form appropriate for the desired mode of administration. The pharmaceutical formulations of the present invention may be administered by any suitable route including oral, rectal, nasal, topical (including buccal and sublingual), vaginal, and parenteral (including subcutaneous, intramuscular, intravenous, and intradermal). It will be appreciated that the route of administration may vary with the condition and age of the recipient, the nature of the condition to be treated, and the given compound(s) of the present invention. In some embodiments, the route of administration is oral. In some embodiments, the one or more ketobutyrate compounds are provided in the form of a foodstuff.

It will be appreciated that the actual dosages of the ketobutyrate compounds used in the pharmaceutical formulations will vary according to the particular compound(s) being used, the particular composition formulated, the mode of administration, and the particular site, subject, and disease being treated. Optimal dosages for a given set of conditions may be ascertained by those skilled in the art using dosage determination tests in view of the experimental data for a given compound. Administration of prodrugs may be dosed at weight levels that are chemically equivalent to the weight levels of the fully active forms.

Pharmaceutical formulations of this invention comprise a therapeutically effective amount of one or more compounds of the present invention, and an inert, pharmaceutically acceptable carrier or diluent. As used herein the language "pharmaceutically acceptable carrier" is intended to include any and all solvents, dispersion media, coatings, antibacterial, and antifungal agents, isotonic and absorption delaying agents, and the like, compatible with pharmaceutical administration. The pharmaceutical carrier employed may be either a solid or liquid. Exemplary of solid carriers are lactose, sucrose, talc, gelatin, agar, pectin, acacia, magnesium stearate, stearic acid, and the like. Exemplary of liquid carriers are syrup, peanut oil, olive oil, water, and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate, and the like. The use of such media and agents for pharmaceutically active substances is known in the art.

Toxicity and therapeutic efficacy of ketobutyrate compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds exhibiting large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

The following examples are intended to illustrate but not to limit the invention.

EXAMPLES

α-KB Extends Both the Mean and Maximum Lifespan of Adult *C. elegans*

To show that α-KB extends lifespan extension, the following experiment was conducted. *C. elegans* were synchronized by performing either a timed egg lay or an egg preparation (mix <100 gravid worms in 70 μl M9 buffer, 25 μl bleach, and 5 μl 10 N NaOH). Once the worms reached adulthood, they were picked onto NGM treatment plates containing 1.5% dimethyl sulfoxide (DMSO; Sigma D8418), 49.5 μM 5-fluoro-2'-deoxyuridine (FUDR, Sigma F0503), 50 μg/ml ampicillin, and α-KB (Sigma K401). Plates containing α-KB were adjusted to pH 6.0 (i.e., the same pH as the control plates) by the addition of NaOH. Treatment plates were seeded with OP50 *E. coli* as the *C. elegans* food source. To assess the survival of the worms, the animals were prodded with a platinum wire every 2-3 days, and those that failed to respond were scored as dead. Worms were moved to new plates every 4 days. All lifespan experiments were conducted at 20° C.

FIG. 1 shows that α-KB extends the lifespan of subjects as compared to the average lifespan of untreated control subjects.

α-KB Specifically Inhibits NADH Dehydrogenase

To show that α-KB inhibits NADH dehydrogenase, the following experiment was conducted. Animal studies were performed under approved UCLA animal research protocols. Mitochondria from 3-month-old C57BL/6 mice were isolated. Briefly, livers were extracted, minced at 4° C. in MSHE+BSA (70 mM sucrose, 210 mM mannitol, 5 mM HEPES, 1 mM EGTA, and 0.5% fatty acid free BSA, pH 7.2), and rinsed several times to remove blood. All subsequent steps were performed on ice or at 4° C. The tissue was disrupted in 10 volumes of MSHE+BSA with a glass Dounce homogenizer (5-6 strokes) and the homogenate was centrifuged at 800×g for 10 minutes to remove tissue debris and nuclei. The supernatant was decanted through a cell strainer and centrifuged at 8,000×g for 10 minutes. The dark mitochondrial pellet was resuspended in MSHE+BSA and re-centrifuged at 8,000×g for 10 minutes. The final mitochondrial pellet was resuspended in 30 μl of MAS buffer (70 mM sucrose, 220 mM mannitol, 10 mM $KH_2PO_4$, 5 mM $MgCl_2$, 2 mM HEPES, 1 mM EGTA, and 0.2% fatty acid free BSA, pH 7.2). Isolated mitochondrial respiration was measured by running coupling and electron flow assays as described.

For the coupling assay, 17 μg of mitochondria in complete MAS buffer (MAS buffer supplemented with 10 mM succinate and 2 μM rotenone or supplemented with 10 mM sodium pyruvate and 2 mM malate) were seeded into a XF24 Seahorse plate by centrifugation at 2,000 g for 20 minutes at 4° C. Just before the assay, the mitochondria were supplemented with complete MAS buffer for a total of 500 μl (with 1% DMSO or α-KB), and warmed at 37° C. for 30 minutes before starting the OCR measurements. Mitochondrial respiration begins in a coupled state 2; state 3 is initiated by 2 mM ADP; state 4o (oligomycin insensitive, that is, complex V independent) is induced by 2.5 μM oligomycin; and state 3u (FCCP-uncoupled maximal respiratory capacity) by 4 μM FCCP (Carbonyl cyanide 4-(trifluoromethoxy)phenylhydrazone, ab120081, Abcam). Finally, 1.5 μg mL antimycin A was injected at the end of the assay.

For the electron flow assay, the MAS buffer was supplemented with 10 mM sodium pyruvate (Complex I substrate), 2 mM malate (Complex II inhibitor) and 4 μM FCCP, and the mitochondria are seeded the same way as described for the coupling assay. After basal readings, the sequential injections were as follows: 2 μM rotenone (Complex I inhibitor), 10 mM succinate (Complex II substrate), 4 μM antimycin A (Complex III inhibitor), and 10 mM/100 μM ascorbate/tetramethylphenylenediamine (Complex IV substrate).

Results show that α-KB only inhibits state 3 and state 3u respiration when respiration is driven by NADH dehydrogenase substrates (Pyruvate and Malate). Consistently, α-KB only inhibits NADH dehydrogenase activity in the electron flow assay.

To study the effect of α-KB on mitochondrial respiration, coupling and electron flow assays were performed using isolated mitochondria. Mitochondria were isolated from mouse liver as described earlier. The final mitochondrial pellet was resuspended in 30 μl of MAS buffer (70 mM sucrose, 220 mM mannitol, 10 mM $KH_2PO_4$, 5 mM $MgCl_2$, 2 mM HEPES, 1 mM EGTA, and 0.2% fatty acid free BSA, pH 7.2).

Mitochondrial respiration was measured by running coupling and electron flow assays. For the coupling assay, 20 μg of mitochondria in complete MAS buffer (MAS buffer supplemented with 10 mM succinate and 2 μM rotenone or 10 mM pyruvate and 2 mM malate) were seeded into a XF24 Seahorse plate by centrifugation at 2,000 g for 20 minutes at 4° C. Just before the assay, the mitochondria were supplemented with complete MAS buffer for a total of 500 μl (with 1% DMSO or α-KB), and warmed at 37° C. for 30 minutes before starting the OCR measurements. Mitochondrial respiration begins in a coupled state 2; state 3 is initiated by 2 mM ADP; state 4o (oligomycin insensitive, that is, complex V independent) is induced by 2.5 μM oligomycin; and state 3u (FCCP-uncoupled maximal respiratory capacity) by 4 μM FCCP. Finally, 1.5 μg/mL antimycin A was injected at the end of the assay.

For the electron flow assay, the MAS buffer was supplemented with 10 mM sodium pyruvate (Complex I substrate), 2 mM malate (Complex II inhibitor) and 4 μM FCCP, and the mitochondria were seeded the same way as described for the coupling assay. After basal readings, the sequential injections were as follows: 2 μM rotenone (Complex I inhibitor), 10 mM succinate (Complex II substrate), 4 μM antimycin A (Complex III inhibitor) and 10 mM/100 µM ascorbate/tetramethylphenylenediamine (Complex IV substrate).

Findings

When respiration is driven by NADH dehydrogenase (supplemented with NADH dehydrogenase substrates, pyruvate and malate), there is a significant decrease in ADP-induced and FCCP-induced respiration upon α-KB treatment; when Complex II substrate (succinate) is supplemented, there is no effect of α-KB on mitochondrial respiration. These results strongly indicate that NADH dehydrogenase is specifically inhibited by α-KB. This hypothesis is further validated by the electron flow assay, wherein only NADH dehydrogenase related respiration is inhibited by α-KB treatment. A similar endogenous metabolite, (R)-3-hydroxybutyrate (3-HB) does not affect Complex II-driven coupling or any step in electron flow, further indicating the specificity of α-KB in inhibiting NADH dehydrogenase.

Figure 2:
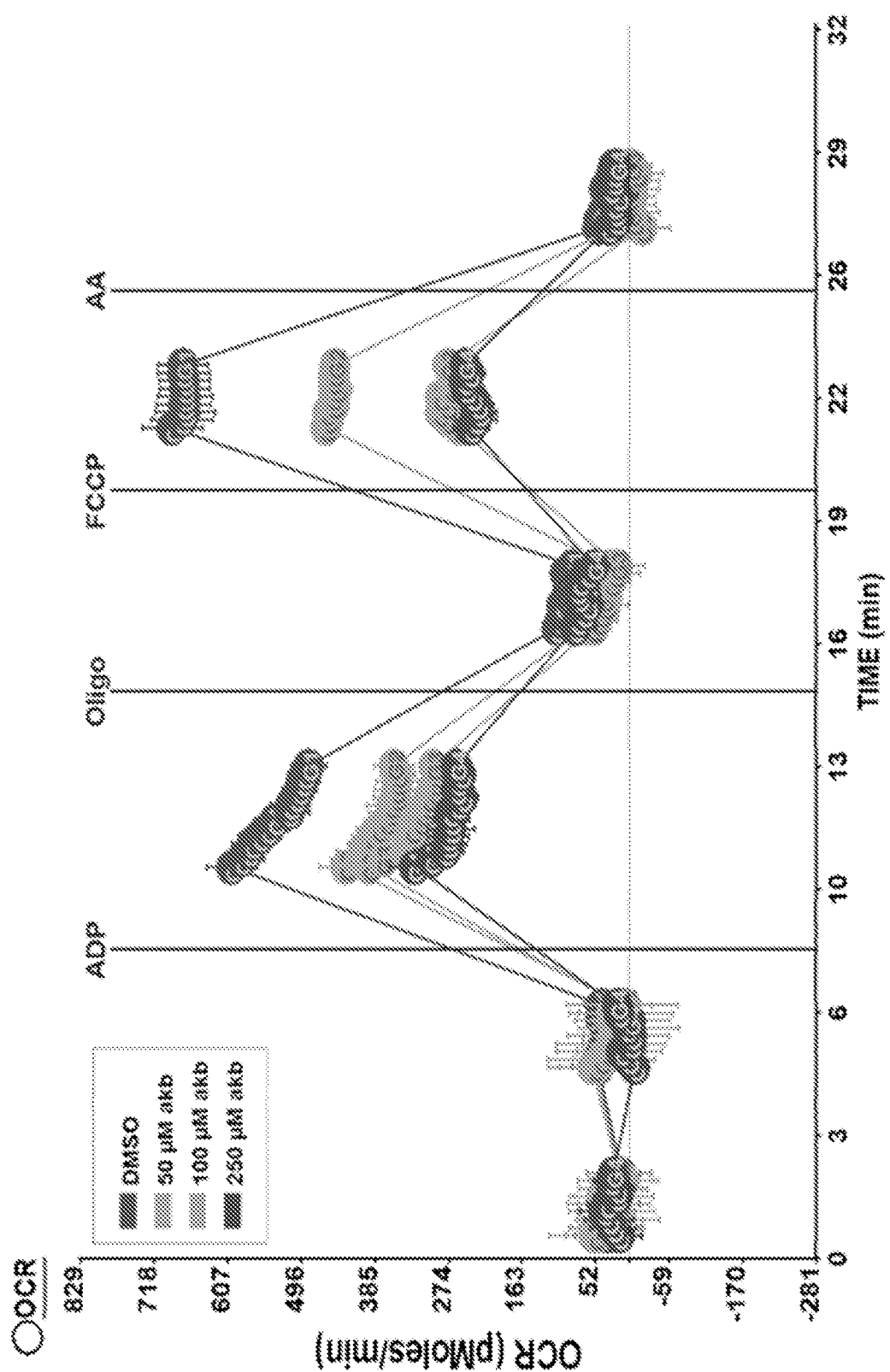
FIG. 2 shows the results of the NADH dehydrogenase (Complex I) driven coupling assay (supplemented with malate and pyruvate). Between the ADP and Oligo points of the graph and between the FCCP and AA points of the graph, the data points from top to bottom are DMSO, 50 μM α-KB, 100 μM α-KB, and 200 μM α-KB.
Figure 3A:
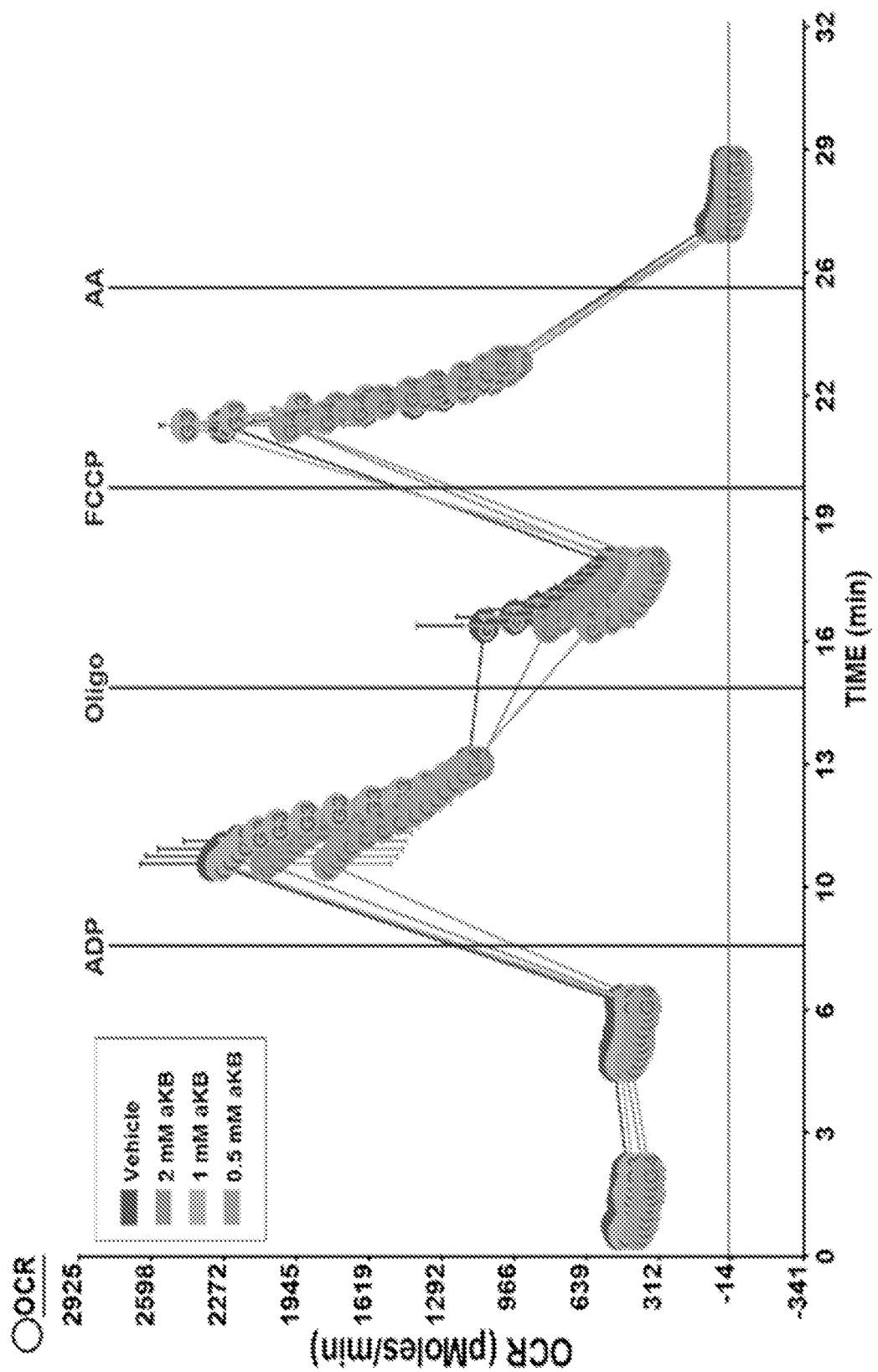
FIG. 3A shows the results of α-KB in the Complex II driven coupling assay (supplemented with succinate and rotenone). Between the ADP and Oligo points of the graph, the top data points are DMSO and the bottom data points are 0.5 mM α-KB.
Figure 3B:
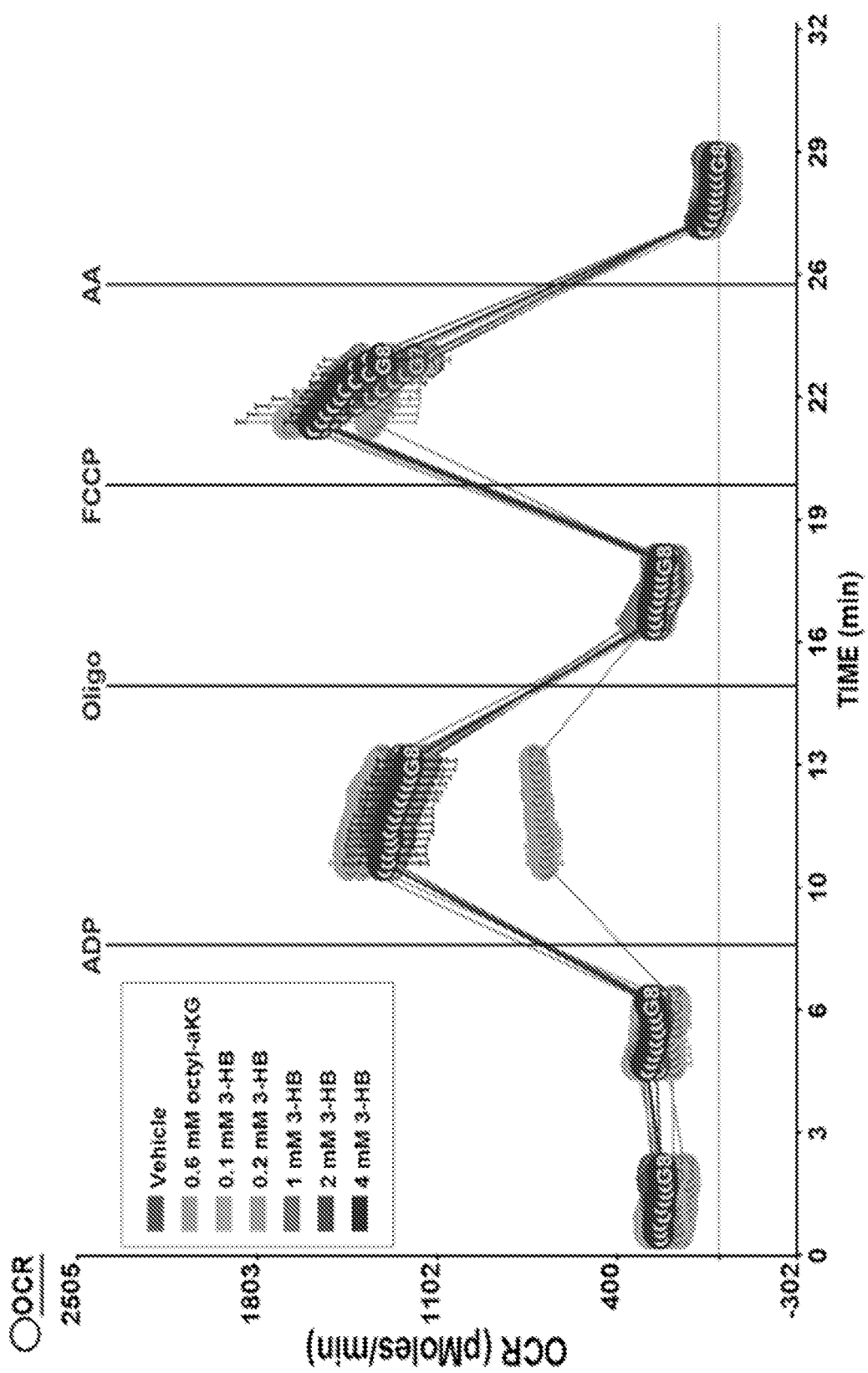
FIG. 3B shows the results of octyl α-KG (octyl α-ketoglutarate) and 3-HB in the Complex II driven coupling assay (supplemented with succinate and rotenone). Between the ADP and Oligo points of the graph, the bottom data points are 0.6 mM octyl α-KG and the top data points are DMSO and 0.1 mM, 0.2 mM, 1 mM, 2 mM, and 4 mM of 3-HB.
Figure 4A:
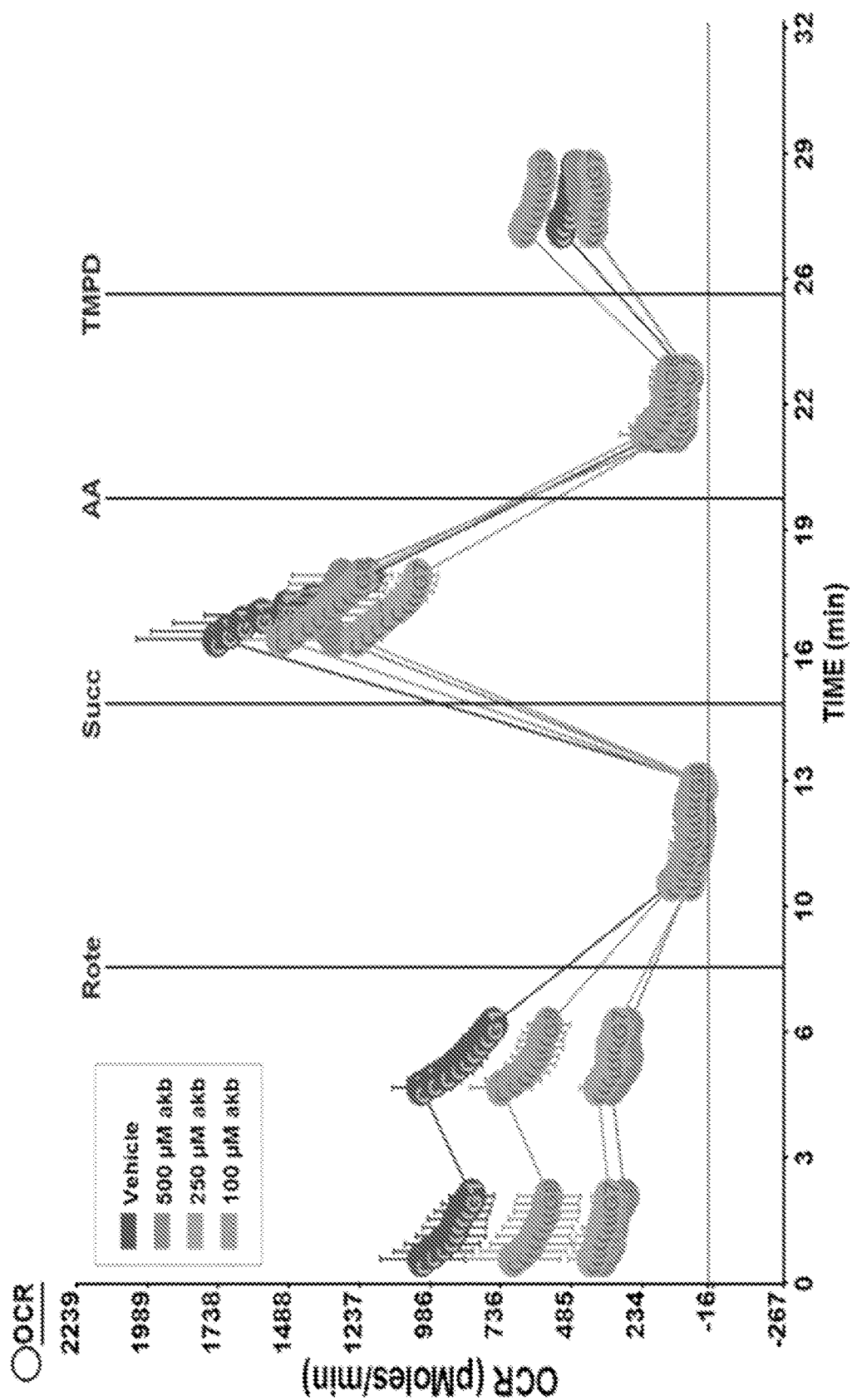
FIG. 4A shows the results of α-KB in the electron flow assay. Before the Rote point of the graph, the top data points are vehicle, the middle data points are 100 μM α-KB, and the bottom data points are 500 μM α-KB and 250 μM α-KB. Between the Succ and AA points of the graph, the top data points are vehicle and the bottom data points are 250 μM α-KB.
Figure 4B:
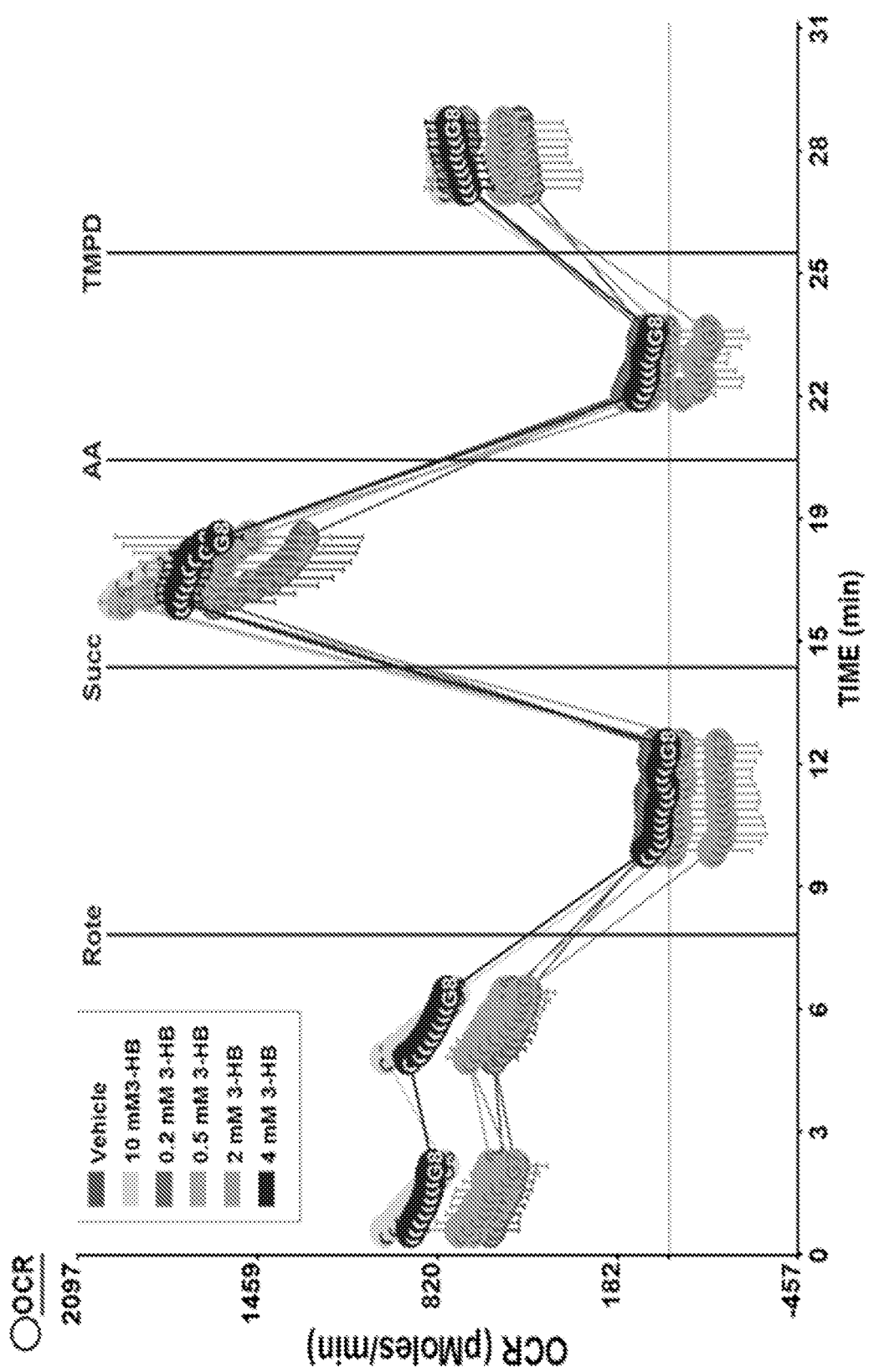
FIG. 4B shows the results of vehicle and 10 mM, 0.2 mM, 0.5 mM, 2 mM, and 4 mM 3-HB in the electron flow assay.

FIG. 2 shows the results of the NADH dehydrogenase (Complex I) driven coupling assay (supplemented with malate and pyruvate). The results of the Complex II driven coupling assay (supplemented with succinate and rotenone) are shown in FIG. 3A (α-KB) and FIG. 3B (3-HB). The results of the electron flow assay are shown in FIG. 4A (α-KB) and FIG. 4B (3-HB).

α-KB Affects Mitochondrial Bioenergetics in Human Cells

α-KB, not only in the isolated mitochondrial model, but also in cellular models, affects mitochondrial bioenergetics. It was found that α-KB inhibits cellular respiration. Moreover, α-KB increases cellular ROS levels. These phenotypes resemble the effects of rotenone, which is a known inhibitor of NADH dehydrogenase. Together these results show that α-KB affects mitochondria, probably through inhibition of NADH dehydrogenase.

Measurement of oxygen consumption rates (OCR). OCR measurements were made using a Seahorse XF-24 analyzer (Seahorse Bioscience). C2C12 Cells were seeded in Seahorse XF-24 cell culture microplates at 30,000 cells per well in DMEM media supplemented with 10% FBS and 10 mM glucose, and incubated at 37° C. and 5% $CO_2$ overnight. Treatment with α-KB or DMSO (vehicle control) was for 1 hour. Cells were washed in unbuffered DMEM medium (pH 7.4, 10 mM glucose) just before measurements, and maintained in this buffer with indicated concentrations of α-KB. OCR was measured three times under basal conditions and normalized to protein concentration per well.

Figure 5A:
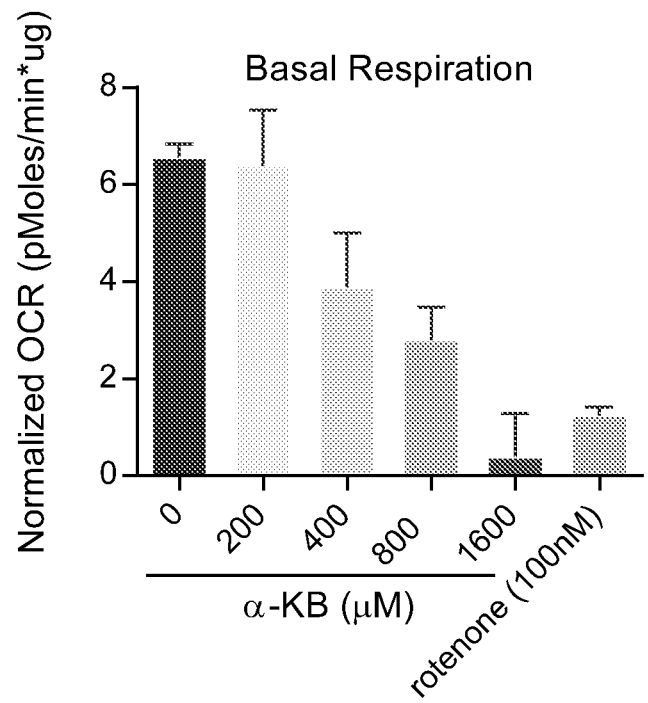
FIG. 5A shows the effect of α-KB on basal respiration.
Figure 5B:
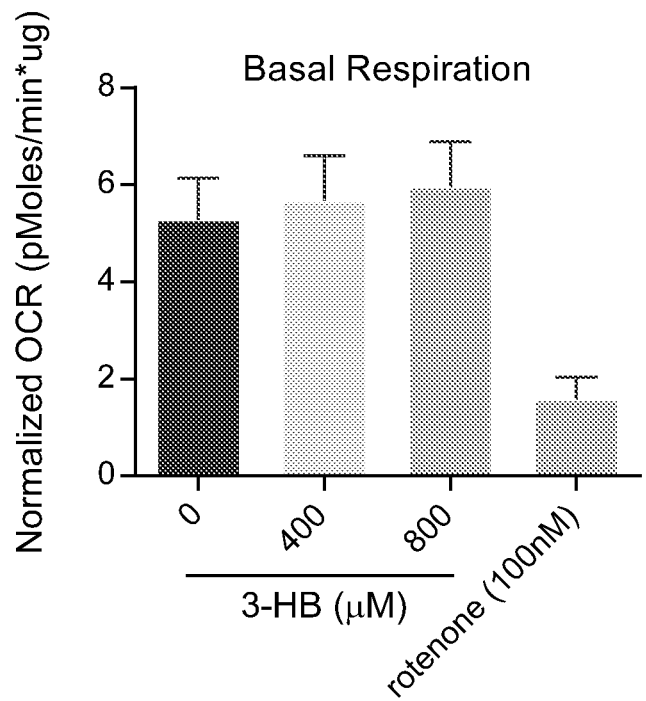
FIG. 5B shows the effect of 3-HB on basal respiration.
Figure 6A:
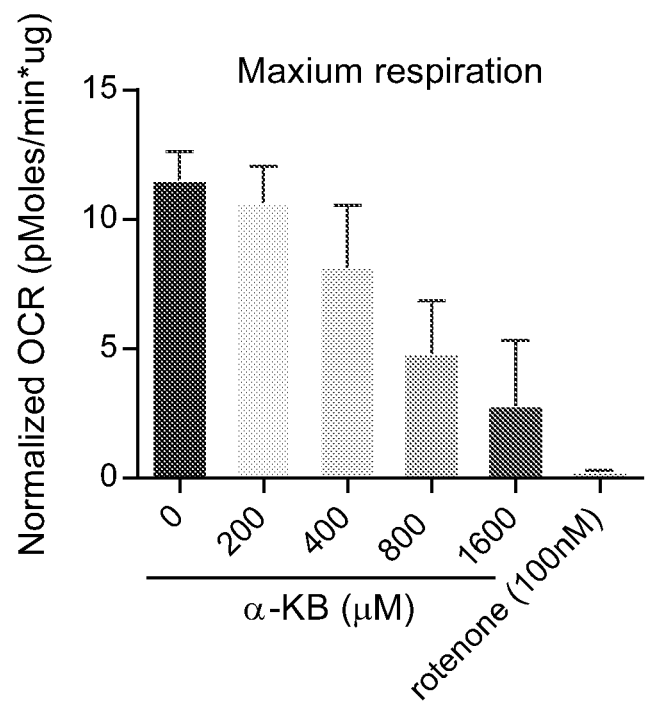
FIG. 6A shows the effect of α-KB on maximal respiration (mitochondrial respiration upon FCCP treatment).
Figure 6B:
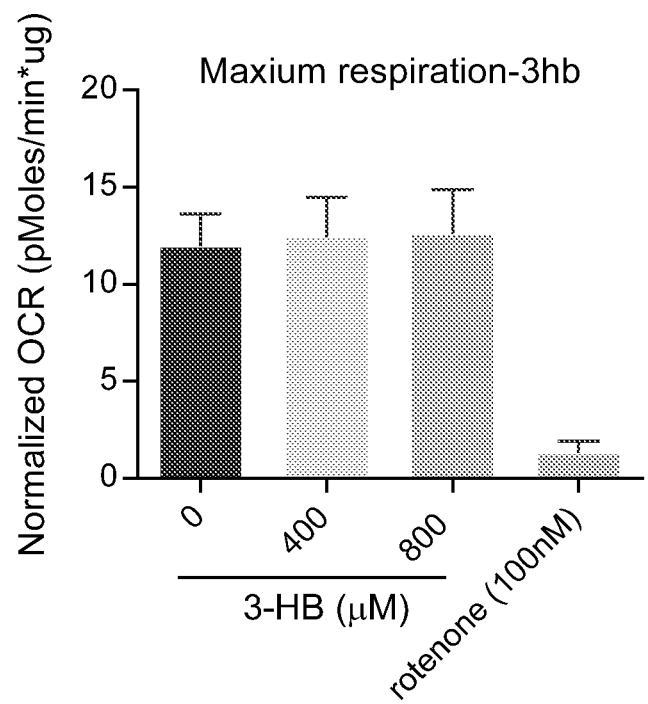
FIG. 6B shows the effect of 3-HB on maximal respiration (mitochondrial respiration upon FCCP treatment).

Upon α-KB treatment, basal respiration (FIG. 5A) and maximal respiration (mitochondrial respiration upon FCCP treatment) (FIG. 6A) are both inhibited, similar to rotenone treatment. As shown in FIGS. 5B and 6B, 3-HB again does not have any effect in this assay.

Measurement of ROS. C2C12 cells were seeded in 96-well plates at density of 250,000 cells/mL. Reactive oxygen species (ROS) levels were measured using 2′, 7′-dichlorodihydrofluorescein diacetate (H2DCF-DA) after 3 hours of drug treatment.

Figure 7:
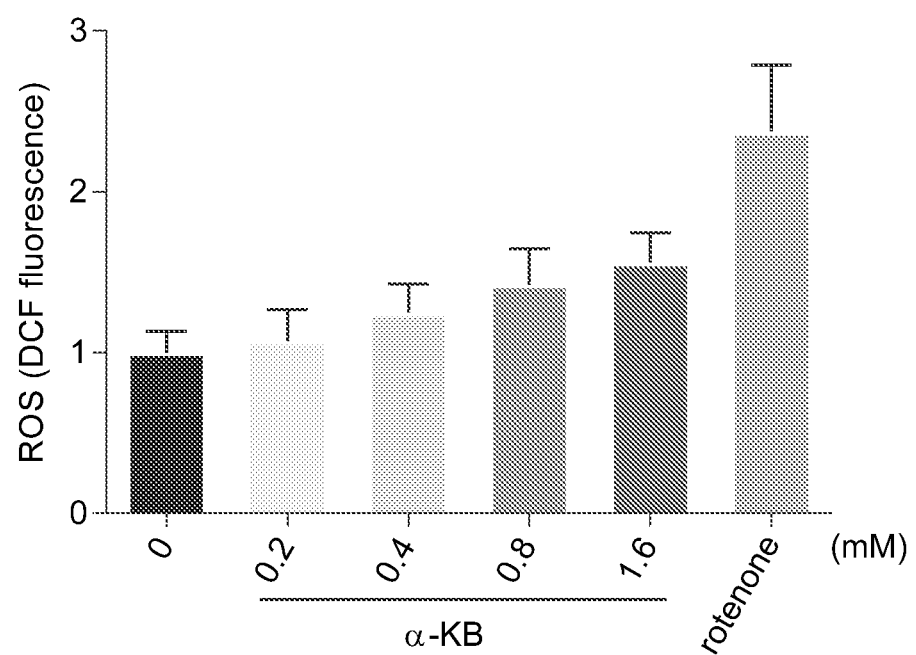
FIG. 7 shows that α-KB increases the cellular ROS in a dose dependent manner.

As shown in FIG. 7, α-KB increases the cellular ROS, similarly as rotenone. This further supports the hypothesis that α-KB inhibits the NADH dehydrogenase.

α-KB Rescues Cardiac Hypertrophy and Heart Failure in Mouse Models

Using cellular and animals models in collaboration with Jake Lusis, Meisheng Jiang and Yibin Wang at UCLA, it was found that α-KB exhibits promising activities against cardiac hypertrophy induced by isoproterenol and by transverse aortic constriction (TAC). For example, administration of α-KB to C57BL/6 mice rescues TAC induced cardiac hypertrophy heart failure. Surgical procedure was performed one day before treatment with vehicle or α-KB. Cardiac output was assessed 3 weeks post-treatment by determining the cardiac ejection fraction (EF) by echo. The EF was decreased in the α-KB-treated mice (0.168±0.023) versus vehicle-treated mice (0.218±0.014), P<0.05.

In additional experiments, cardiomyocytes of neonatal rats were isolated by collagenase digestion and cultured overnight in DMEM containing 10% FCS, and then culture medium was changed to serum-free high glucose DMEM with supplement of ITS (insulin, transferrin, and sodium-selenite).

Catecholamine-induced cardiac hypertrophy. Hypertrophy of cardiomyocytes was induced by treating the cells with 1 mM isoproterenol (ISO) or phenylephrine (PE) for 48 hours. α-KB (1 mM) completely abolished ISO- and PE-induced hypertrophy, as well as suppressed the induced overexpression of ANF and BNP, which are hypertrophy associated markers.

Transverse aortic constriction (TAC) in mice was used to induce pressure overload-induced heart failure and cardiac hypertrophy. TAC surgical procedure was performed one day before treatment with vehicle or α-KB. C57BL/6 male mice were treated with α-KB at 30 mg/kg body weight per day in drinking water. Cardiac output was assessed 3 weeks post-treatment by determining the cardiac ejection fraction (EF) measured by Echo.

The EF for the control mice at three weeks after the TAC procedure was 0.218±0.014 (n=8, including 5 tested in previous experiments), and for α-KB treated animals was 0.268±0.023 (n=7) (Mean, SEM), P<0.05. At the end of experiment (5 weeks), the heart (mg)/body (g) ratios were 13.23±1.0 (n=2) for the control group, and 10.72±1.98 (n=6) (Mean, STEDV) for the α-KB treated group, P=0.147. Thus, α-KB significantly enhances the cardiac output in the TAC-induced heart failure mouse model, and also appeared to decrease mortality in these mice.

α-KB Reverses Age-Related Symptoms in Aged Mice

Aged mice (22-23 month old C57BL/6J), including both males and females, were fed either water or α-KB (8 mM in drinking water or 90 mg/kg body weight) for 7 months. During the study period, no adverse effects of α-KB were observed in treated animals. A-KB treated mice exhibited normal behavior and physical activities during the test period compared to untreated control animals. Mice were examined at least twice a week for signs of ill health, and severely sick or immobilized mice were subject to termination. The lifespan of α-KB treated male group was extended. All the males in untreated control group (5 of 5) died or were terminated due to severe illness before the completion of the 7 months test. Remarkably, most of the males in the α-KB treated group (4 of 5) lived healthily and were still in excellent health at the end of the 7 months study period.

Figure 8:
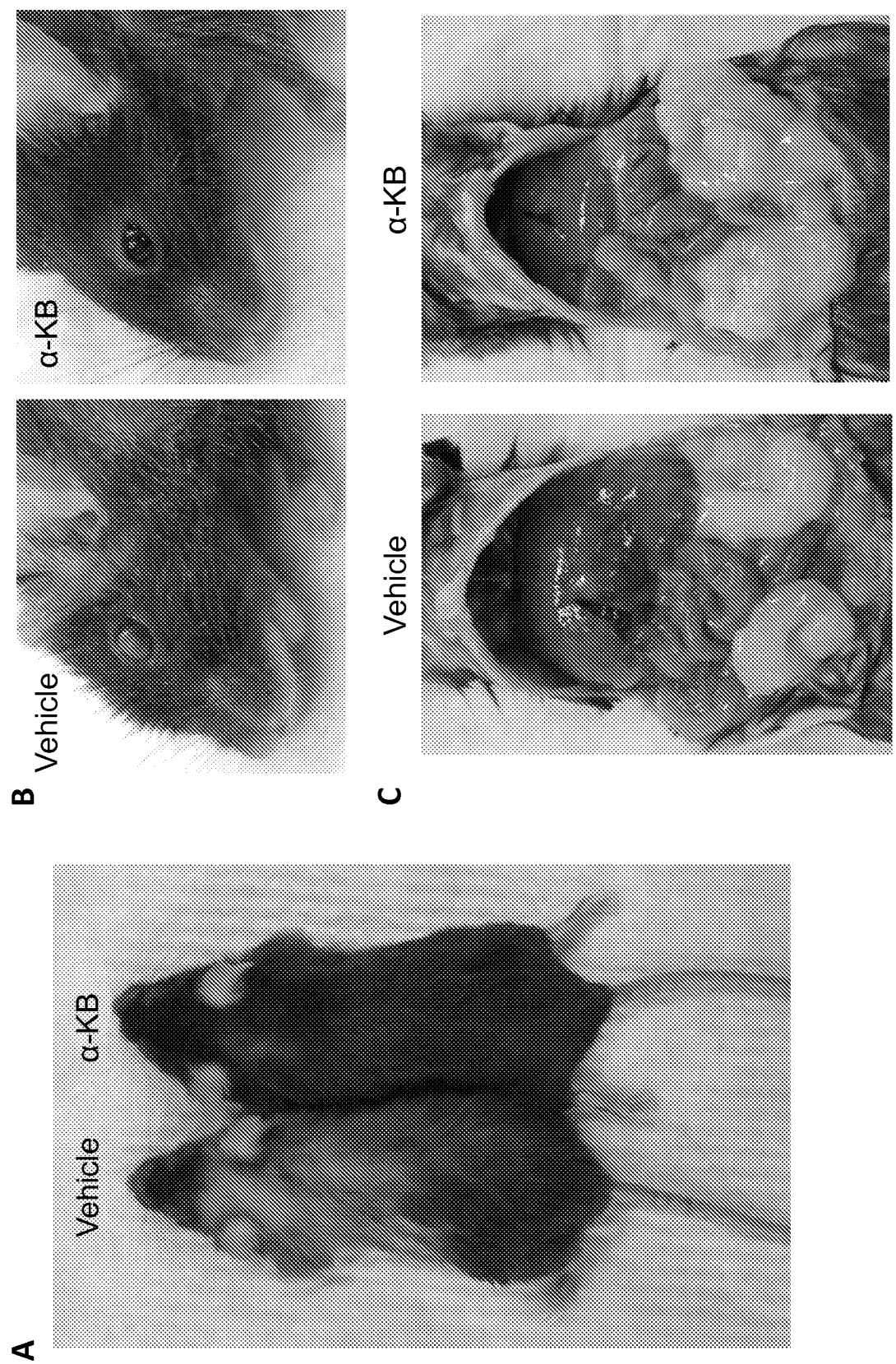
FIG. 8, panels A-C, show the absence of age-related symptoms in aged mice treated with α-KB. Panel A shows that mice treated with α-KB have improved hair density (or reduced hair loss) as compared to untreated control mice. Panel B shows that α-KB treated mice have no cataracts and exhibit reduced hair graying as compared to untreated control mice. Panel C shows α-KB treated mice had healthy livers (color, size, fat content) as compared to untreated controls.

Although the lifespan of females in treated and untreated groups were indistinguishable, the female mice treated with α-KB exhibited improved hair and fur appearance starting at about 2 to about 3 months after the animals received α-KB treatment (FIG. 8, panel A, shows them at 7 months post treatment). Hair density in the treated female group was higher than that in the untreated control (FIG. 8, panel A). The gray hair in α-KB treated group was reduced compared to the untreated group (FIG. 8, panel B). For the treated male group, the effect on gray hair and hair density appeared to be minimal. α-KB treatment also greatly improved liver appearance. In aged untreated animals, the liver lost its characteristic reddish color and assumed a yellowish tint.

Livers from the both male and female treated animals exhibited healthy appearance of reddish color without any yellowish tint (FIG. 8, panel C). Taken together, these results suggest α-KB possesses anti-aging property to delay or even reverse the aging process in mammals.

α-KB for Reducing Ischemia Reperfusion Injury and Myocardial Infarction

Figure 9A:
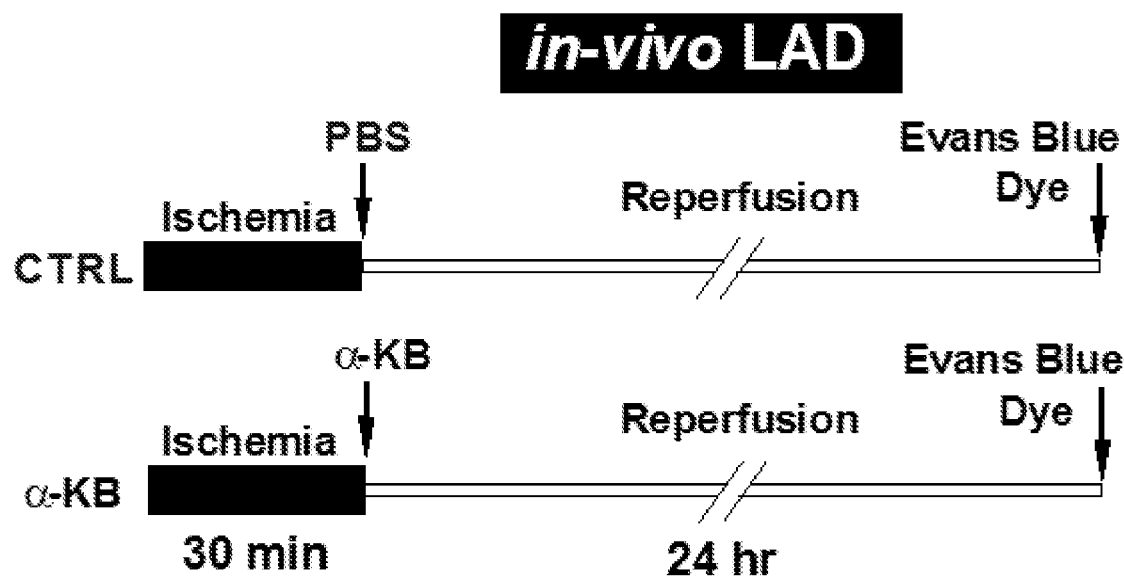
FIGS. 9A-9C show that post-ischemic administration of α-KB reduces the myocardial infarct size. **P<0.01, n=about 5-6 mice per group.
Figure 9B:
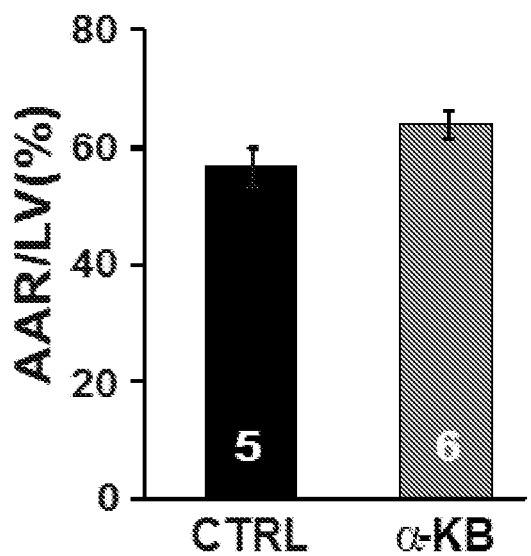
Figure 9C:
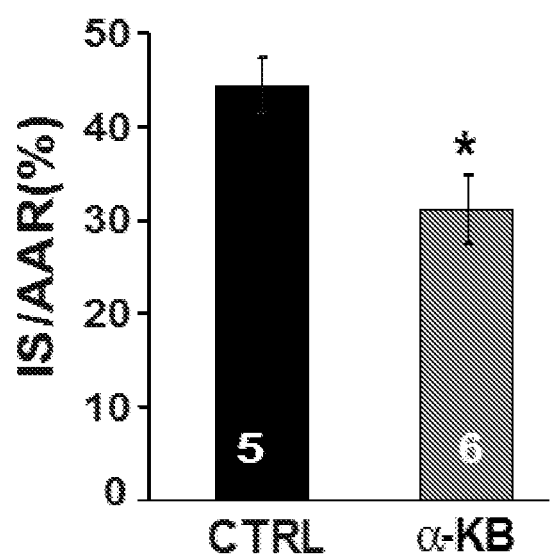
Figure 10:
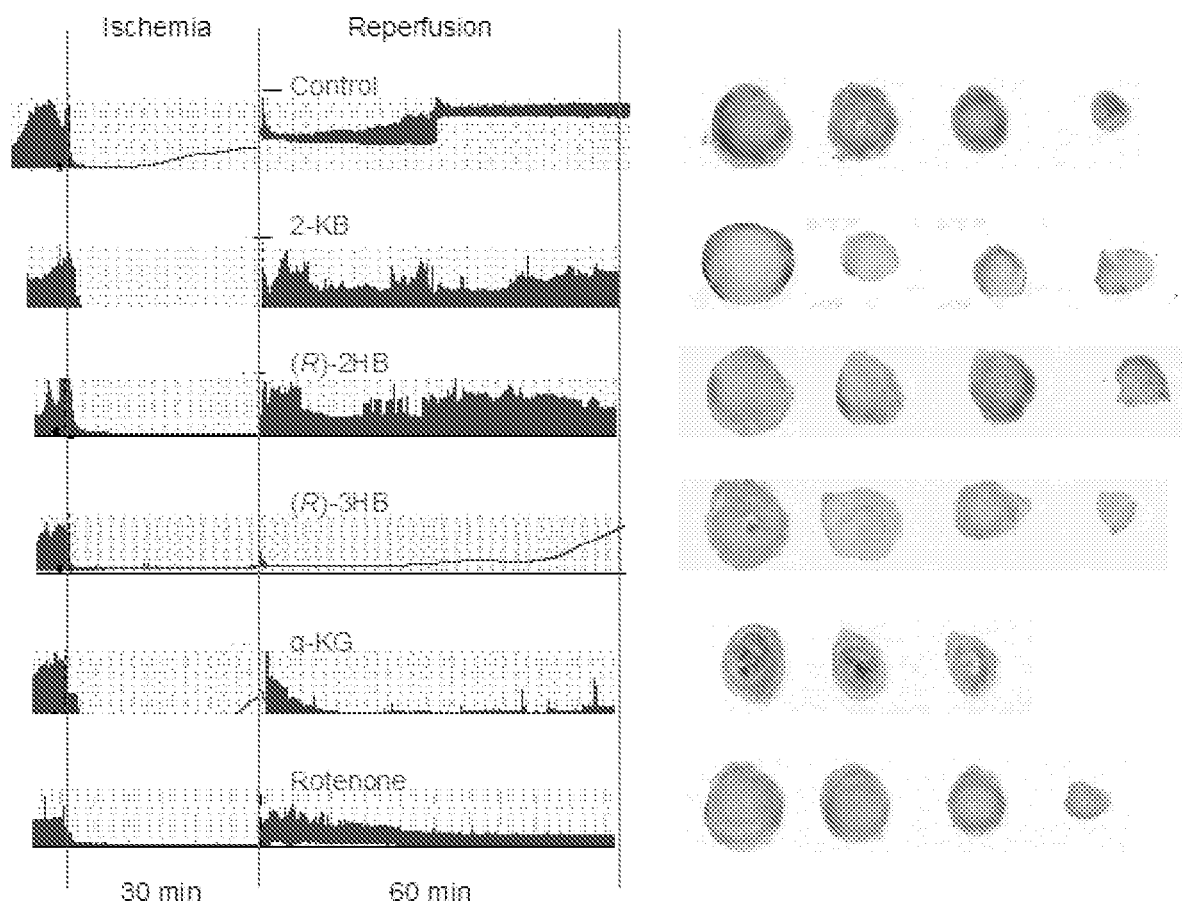
FIG. 10, left, shows that post-ischemic administration of 2-KB restores heart function after ischemia. Isolated hearts were subjected to 30 minutes ischemia followed by 60 minutes of reperfusion with control buffer, 2-KB, (R)-2-hydroxybutyrate, (R)-3-hydroxybutyrate (also known as ketone body), α-KG, and the Complex I inhibitor rotenone. LVDP is shown as a function of time.

To examine the cardioprotective role of α-KB, an in vivo model of ischemia reperfusion injury was used. The left coronary artery was occluded for 30 minutes in male mice followed by 24 hours of reperfusion. One single bolus of PBS (vehicle control) or α-KB (800 μM) was applied through the tail vein at the onset of reperfusion (FIG. 9A). The area at risk (AAR) to left ventricle ratio was similar in both groups, 64.1±2.3 in α-KB (n=6) vs. 56.8±3.3 (n=5) in control treatment, indicating that the two groups were subjected to a comparable degree of ischemic risk (FIG. 9B). However, the infarct size was significantly smaller in the α-KB group compared to the control; the ratio of infarct size to AAR was 31.2±3.6 in α-KB (n=6) vs. 44.5±3.0 in the control (n=5), P=0.02 (FIG. 9C). FIG. 10 shows the infarct sizes resulting from treatment before reperfusion.

α-KB Delays Paralysis in a C. elegans Alzheimer's Disease Model

Figure 11:
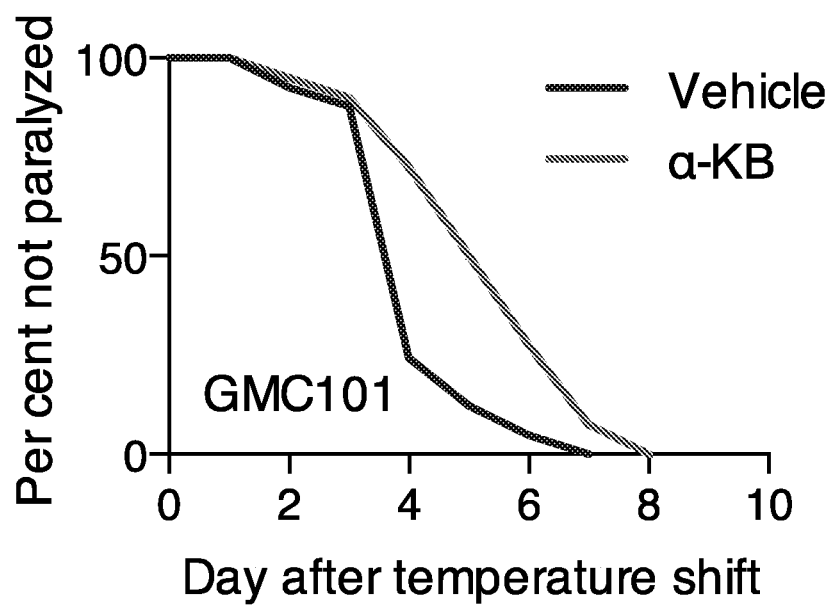
FIG. 11 shows that α-KB delays paralysis in *C. elegans* compared to vehicle treated worms.

To show that α-KB delays paralysis in a C. elegans model of Alzheimer's disease, the GMC101 C. elegans strain that was developed by Gawain McColl at the University of Melbourne, Australia, which expresses the full length human amyloid-beta 1-42 protein in the body wall muscle cells, leading to a fully-penetrant age-progressive paralysis was used. Worms were age-synchronized by performing a timed egg lay for 3 hours with about 100 gravid adults and the eggs placed in a 20° C. incubator. Once the eggs had developed to the L4 stage at 42 hours post egg lay, they were picked onto NGM treatment plates containing 49.5 μM 5-fluoro-2'-deoxyuridine (FUDR, Sigma F0503) to prevent progeny production and either 4 mM α-KB or vehicle (water) control. The worms were then shifted to 30° C. to induce amyloid-beta aggregation and paralysis. Worms were assessed for paralysis daily, beginning on the second day of treatment, by the failure to perform whole body bends and significantly move forwards and backwards upon gentle prodding with a platinum wire. Most paralyzed worms could still move their heads and part of their body. All worms were transferred to fresh treatment plates on Day 4. As shown in FIG. 11, 4 mM α-KB delayed paralysis by up to 37% compared to vehicle treated worms.

α-KB Helps Reduce HCV Infection

Figure 12A:
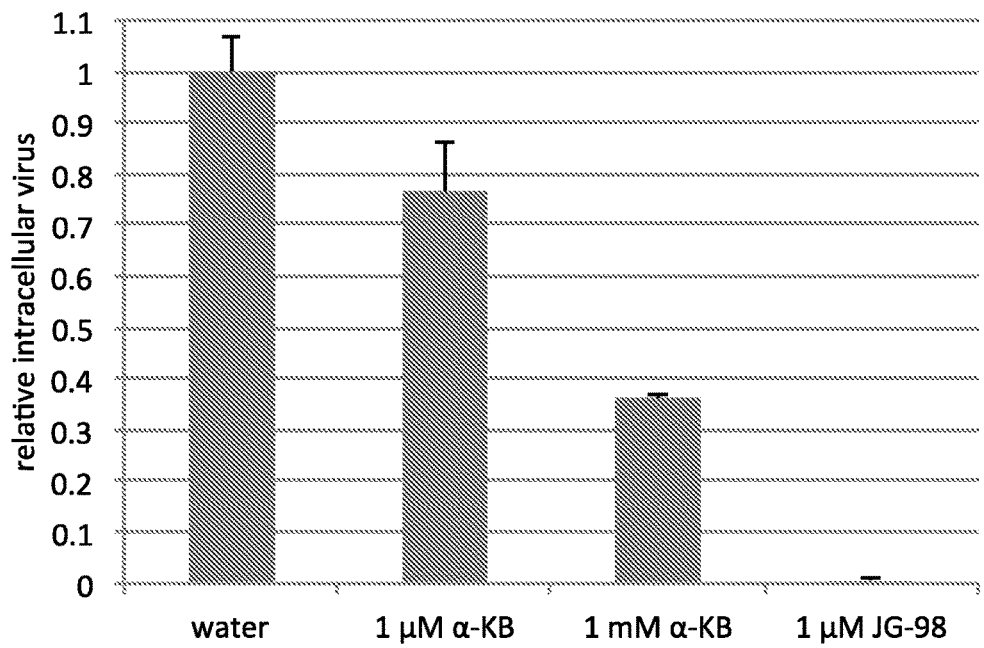
FIG. 12A shows that α-KB inhibits or reduces HCV infection in a dose dependent manner. Butler, α-KB.
Figure 12B:
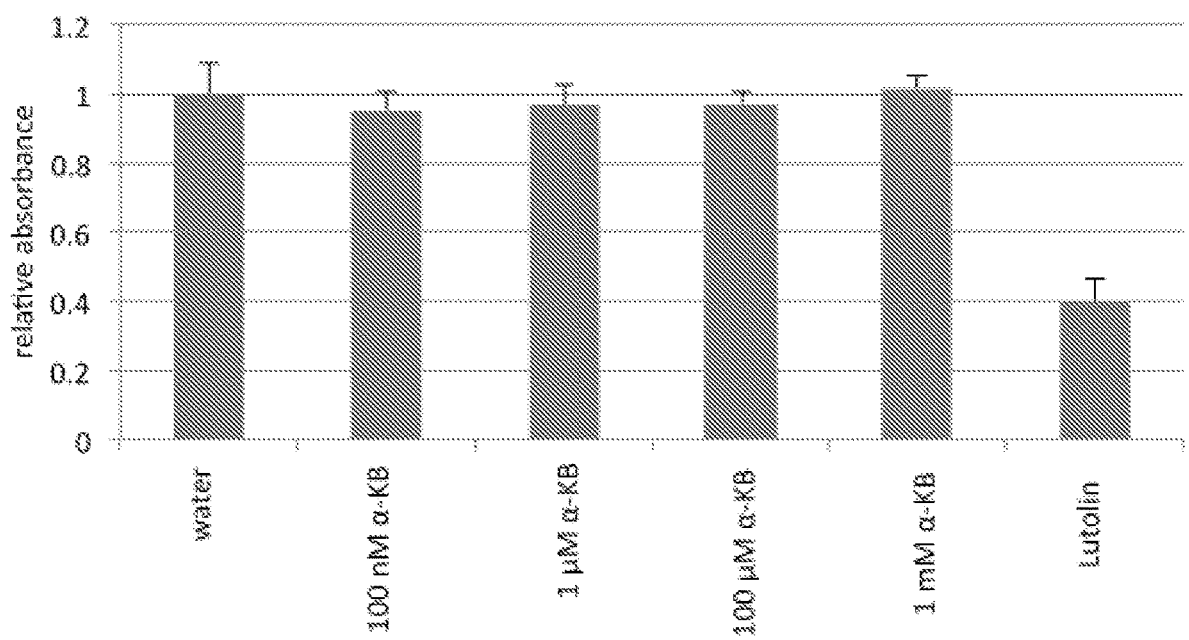
FIG. 12B shows that the inhibition of HCV infection by α-KB is not a result of cytotoxicity. Butler, α-KB.
Figure 13:
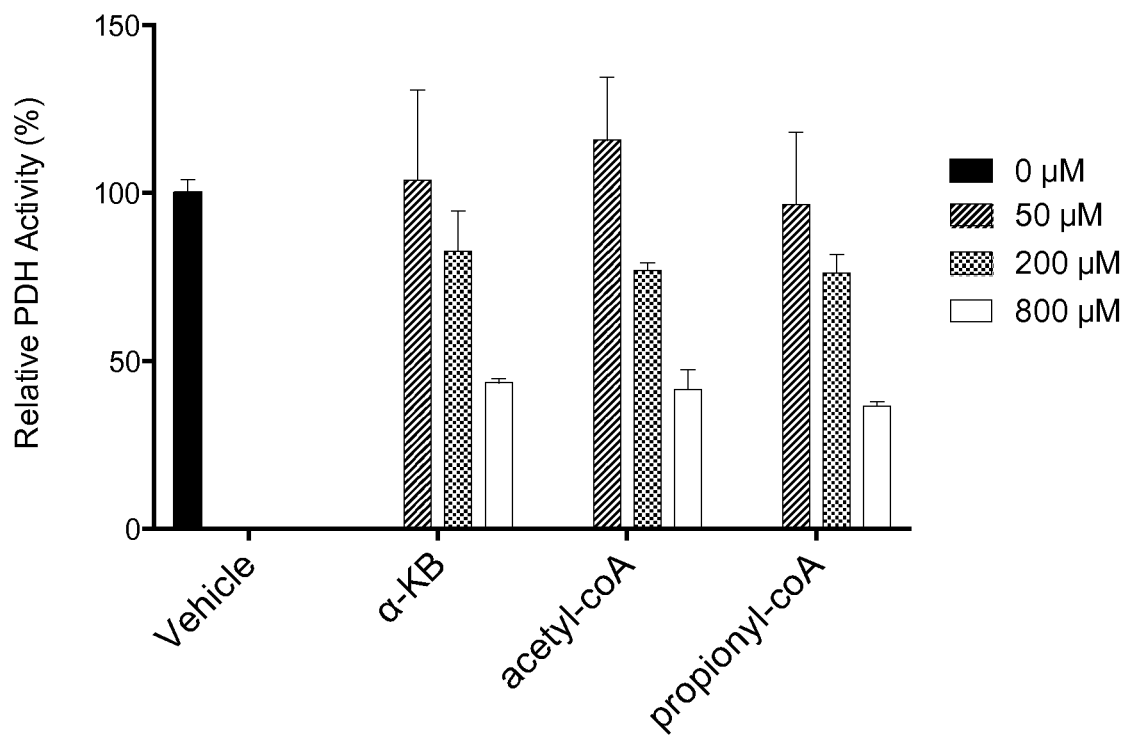
FIG. 13 shows that α-KB inhibits pyruvate dehydrogenase and thereby decreases ETC Complex I activity. In the graph, after the vehicle, the first bars are 50 μM, 200 μM, and 800 μM.
Figure 14:
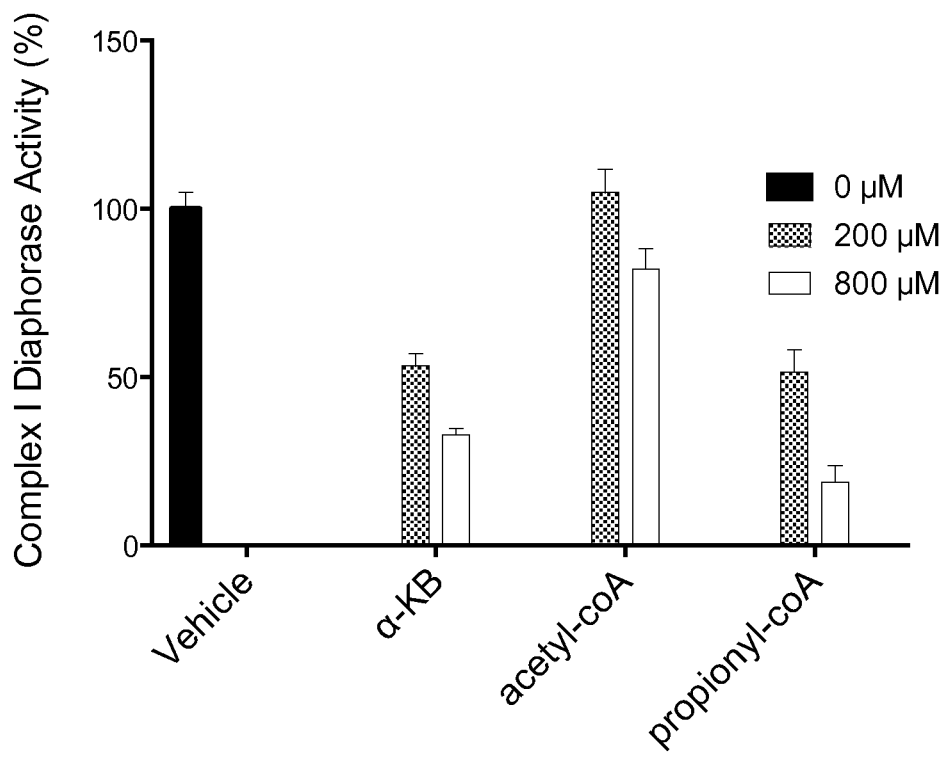
FIG. 14 shows that α-KB directly inhibits ETC Complex I diaphorase (NADH: acceptor oxidoreductase. In the graph, after the vehicle, the first bars are 200 μm and the second bars are 800 μm.

As subjects age, their susceptibility to infection increases. Therefore, to determine whether α-KB reduces ones susceptibility to age-related infection, Huh7.5 cells were infected with the Renilla reporter HCV for 5 hours and subsequently treated with 1 mM and 1 μM of α-KB. 72 hours post treatment, the cells were lysed and luciferase activity was measured. JG-98, which is a suppressor of viral assembly, was used as a positive control and water was used as a negative control. As shown in FIG. 12A, α-KB inhibits or reduces viral infection. To ensure that the anti-viral activity of α-KB is not the result of cytotoxicity, Huh7.5 cells were treated with 1 mM, 100 μM, 10 μM, 1 μM, and 100 nM α-KB. MTT assays were performed every 24 hours up to 72 hours post treatment. Luteolin, an anti-cancer compound which is cytotoxic, was used as a positive control and water was used as a negative control. As shown in FIG. 12B, α-KB is not cytotoxic.

α-KB Inhibits Pyruvate Dehydrogenase, Leading to Decreased ETC Complex I Activity To examine the effect of α-KB on pyruvate dehydrogenase, the Pyruvate Dehydrogenase (PDH) Enzyme Activity Microplate Assay Kit (Abcam, ab109902) was used. The assay was performed according to the protocol provided. Detergent was added to bovine heart mitochondrial lysate (Abcam, ab110338) and followed by an incubation at 4° C. for 20 minutes to release PDH. The sample was then centrifuged at 14,000×g for 10 minutes. Supernatant was diluted with the incubation buffer and added to a PDH antibody-coated 96-well plate. After 3 hours incubation followed by 2× wash with stabilizer buffer, the wells were added with 200 μL of reaction mix containing 10, 20, 50, 200, and 800 μM α-KB or vehicle control (distilled water). Each condition was performed in triplicates. Kinetic measurements of absorbance at 450 nm with 1 minute intervals were taken, and PDH activity was calculated from the slope of the absorbance to time. The readings were normalized to vehicle mean (as 100 percent). As shown in FIG. 13, the normalized activity (percentage) for 200 and 800 μM α-KB treated wells were significantly lower than control: vehicle (water), 100±14.9; 200 μM α-KB, 68.0±11.8, P=0.0408; 800 μM α-KB, 41.6±7.89, P=0.004.

α-KB Directly Inhibits ETC Complex I Diaphorase (NADH: Acceptor Oxidoreductase)

Figure 15A:
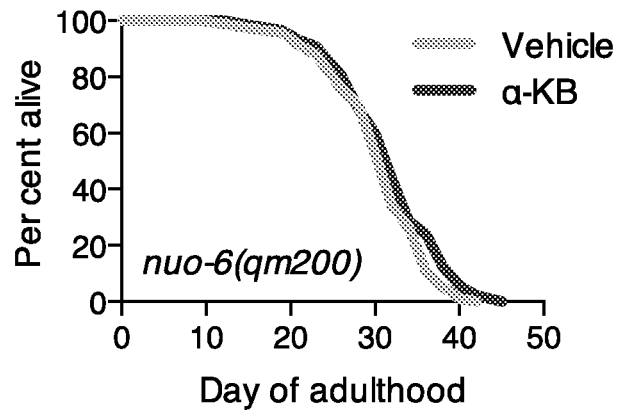
FIG. 15A shows that α-KB does not further increase the lifespan of the long-lived nuo-6(qm200) mutant *C. elegans* strain.
Figure 15B:
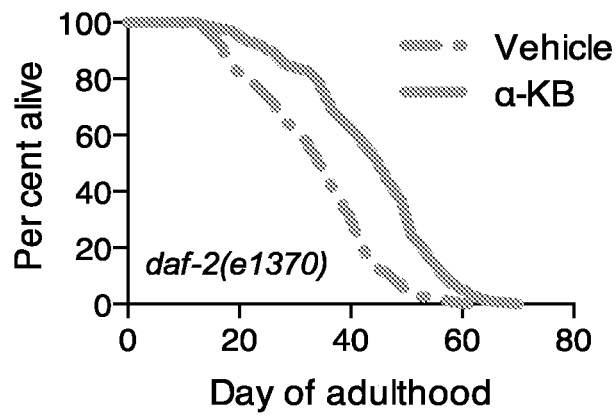
FIG. 15B shows that α-KB increases the lifespan of the even longer-lived daf-2(e1370) mutant *C. elegans* strain.
Figure 15C:
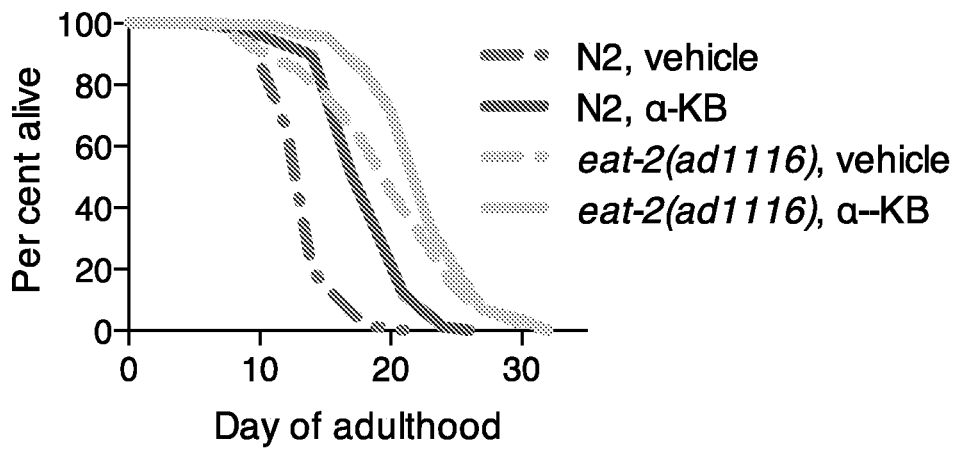
FIG. 15C shows that α-KB increases the lifespan of the long-lived eat-2(ad1116) mutant *C. elegans* strain.

To assess if α-KB can affect the diaphorase (NADH: acceptor oxidoreductase) activity of Complex I, the Complex I Enzyme Activity Microplate Assay Kit (Abcam, ab109721) was used. The assay was performed according to the protocol provided. Bovine Heart Mitochondria lysate (Abcam, ab110338) was added with detergent, followed by incubation on ice for 30 minutes to release Complex I and then centrifuged at 12,000 g, 4° C. for 20 minutes. Supernatant was collected and diluted with the buffer provided and then added to a Complex I antibody-coated 96-well plate. After a 3 hour incubation followed by 2× wash with stabilizer buffer, the wells were added with 200 μL of reaction mix containing 50, 200, or 800 μM α-KB or vehicle control (distilled water). Each condition was performed in triplicates. Kinetic measurements of absorbance at 450 nm with 1 minute intervals were taken, and Complex I diaphorase activity was calculated from the slope of the absorbance to time. The readings were normalized to vehicle mean (as 100 percent).

α-KB does not Extend the Lifespan of the Long-Lived Complex I Mutant C. elegans Strain The nuo-6 gene encodes the C. elegans ortholog of the NDUFB4/B15 subunit of the mitochondrial electron transport chain complex I, also known as the NADH dehydrogenase complex. As shown in FIG. 15A, the nuo-6(qm200) mutant strain has reduced Complex I function and is long-lived compared to wild-type N2 C. elegans. The inability of α-KB to extend the lifespan of the nuo-6(qm200) strain is consistent with an anti-aging mechanism of α-KB mediated through complex I. On the other hand, as shown in FIG. 15B, α-KB does extend the lifespan of the even longer-lived daf-2(e1370) strain, or of the eat-2(ad1116) strain, as shown in FIG. 15C. These findings are important because they demonstrate that the anti-aging effect of α-KB is independent of two major aging pathways, the insulin/IGF-1 signaling pathway (daf-2) and the dietary restriction pathway (eat-2). This not only demonstrates the specificity of lifespan extension through mitochondrial ETC inhibition, but also suggests that α-KB may work synergistically with molecules that extend lifespan through both the insulin/IGF-1 pathway and the dietary restriction pathway.

All scientific and technical terms used in this application have meanings commonly used in the art unless otherwise specified.

As used herein, the term "subject" includes humans and non-human animals. The term "non-human animal" includes all vertebrates, e.g., mammals and non-mammals, such as non-human primates, horses, sheep, dogs, cows, pigs, chickens, and other veterinary subjects and test animals.

The use of the singular can include the plural unless specifically stated otherwise. As used in the specification and the appended claims, the singular forms "a", "an", and "the" can include plural referents unless the context clearly dictates otherwise. The use of "or" can mean "and/or" unless stated otherwise. As used herein, "and/or" means "and" or "or". For example, "A and/or B" means "A, B, or both A and B" and "A, B, C, and/or D" means "A, B, C, D, or a combination thereof" and said "combination thereof" means any subset of A, B, C, and D, for example, a single member subset (e.g., A or B or C or D), a two-member subset (e.g., A and B; A and C; etc.), or a three-member subset (e.g., A, B, and C; or A, B, and D; etc.), or all four members (e.g., A, B, C, and D).

To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A method for reducing infarct size of myocardial tissue in a human, comprising administering to the human a therapeutically effective amount of alpha-ketobutyrate or alpha-ketobutyric acid,
    wherein the infarct size of myocardial tissue in the human after administration of the alpha-ketobutyrate or alpha-ketobutyric acid is reduced as compared to a control,
    wherein the alpha-ketobutyrate or alpha-ketobutyric acid is administered as a daily dose of about 0.01-0.5 grams per kilogram body weight per day, and
    wherein the alpha-ketobutyrate or alpha-ketobutyric acid is administered after a myocardial infarction in the human.

2. The method according to claim 1, wherein the therapeutically effective amount is less than the amount of alpha-ketoglutarate or alpha-ketobutyric acid needed to produce a same observable difference.

3. The method according to claim 1, wherein the therapeutically effective amount is less than half the amount of alpha-ketoglutarate or alpha-ketobutyric acid needed to produce a same observable difference.

4. The method according to claim 1, wherein the therapeutically effective amount is about 1/16 the amount of alpha-ketoglutarate or alpha-ketobutyric acid needed to produce a same observable difference.

5. The method according to claim 1, wherein the therapeutically effective amount is administered as several doses over a given period of time.

6. The method according to claim 1, which comprises increasing alpha-ketobutyrate or alpha-ketobutyric acid levels in the human by about 30-60%.

7. The method according to claim 1, wherein the therapeutically effective amount is administered as a daily dose for a week or more.

8. The method according to claim 1, wherein alpha-ketobutyrate or alpha-ketobutyric acid is administered as a daily dose of about 0.1-0.2 grams per kilogram body weight per day.

9. The method according to claim 1, which comprises increasing alpha-ketobutyrate or alpha-ketobutyric acid levels in the human by about 45-55%.

10. The method according to claim 1, which comprises increasing alpha-ketobutyrate or alpha-ketobutyric acid levels in the human by about 50%.

11. The method of claim 1, wherein the control is an infarct size of myocardial tissue in the human prior to administration of alpha-ketobutyrate or alpha-ketobutyric acid.

12. The method of claim 1, wherein the control is an infarct size of myocardial tissue in an untreated human.

* * * * *